United States Patent
Hayashi

(10) Patent No.: US 11,614,624 B2
(45) Date of Patent: Mar. 28, 2023

(54) DISPLAY APPARATUS

(71) Applicant: SONY SEMICONDUCTOR SOLUTIONS CORPORATION, Kanagawa (JP)

(72) Inventor: Kengo Hayashi, Kanagawa (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 281 days.

(21) Appl. No.: 16/981,458

(22) PCT Filed: Mar. 5, 2019

(86) PCT No.: PCT/JP2019/008613
§ 371 (c)(1),
(2) Date: Sep. 16, 2020

(87) PCT Pub. No.: WO2019/181482
PCT Pub. Date: Sep. 26, 2019

(65) Prior Publication Data
US 2021/0026141 A1 Jan. 28, 2021

(30) Foreign Application Priority Data
Mar. 23, 2018 (JP) .............................. JP2018-056326

(51) Int. Cl.
*G02B 27/01* (2006.01)
*G02B 5/32* (2006.01)
*G02B 25/00* (2006.01)

(52) U.S. Cl.
CPC .......... *G02B 27/0172* (2013.01); *G02B 5/32* (2013.01); *G02B 25/001* (2013.01); *G02B 2027/0174* (2013.01)

(58) Field of Classification Search
CPC ...... G02B 27/0172; G02B 5/32; G02B 25/21; G02B 2027/0174; G02B 2027/0187;
(Continued)

(56) References Cited

U.S. PATENT DOCUMENTS

| | | | |
|---|---|---|---|
| 5,394,202 A | 2/1995 | Deering | |
| 5,714,967 A | 2/1998 | Okamura et al. | |
| 6,043,799 A * | 3/2000 | Tidwell | G02B 27/0093 |
| | | | 359/630 |
| 6,353,422 B1 | 3/2002 | Perlman | |

(Continued)

FOREIGN PATENT DOCUMENTS

| CN | 101583898 A | 11/2009 |
|---|---|---|
| CN | 102289073 A | 12/2011 |

(Continued)

OTHER PUBLICATIONS

International Search Report and Written Opinion prepared by the Japanese Patent Office dated May 21, 2019, for International Application No. PCT/JP2019/08613.

*Primary Examiner* — Collin X Beatty
(74) *Attorney, Agent, or Firm* — Sheridan Ross P.C.

(57) ABSTRACT

A display apparatus that can surely make an image reach an observer's pupil without imposing a burden on the observer. The apparatus includes: an eyepiece optical system; and an image display apparatus including an image forming apparatus and a transfer optical system. The eyepiece optical system and the image display apparatus are spatially separated from each other, the eyepiece optical system forms an image from the transfer optical system on a retina of an observer, the image display apparatus further includes a first position detection apparatus that detects a position of the eyepiece optical system, a second position detection apparatus that detects a position of a pupil of the observer. On the
(Continued)

basis of detected positional information of the eyepiece optical system and the pupil, the transfer optical system is controlled such that the image incident from the image forming apparatus reaches the eyepiece optical system.

19 Claims, 14 Drawing Sheets

(58) Field of Classification Search
CPC .......... G02B 2027/0198; G02B 27/017; G02B 2027/011; G02B 2027/0132; G02B 2027/0136; G02B 2027/0178; G02B 26/10; G02B 26/105; G02B 27/0093; G02B 27/0101; G02B 30/24
USPC .......................................................... 359/13
See application file for complete search history.

(56) References Cited

U.S. PATENT DOCUMENTS

| | | | |
|---|---|---|---|
| 2002/0051118 A1* | 5/2002 | Takagi | G02B 27/0172 348/E13.047 |
| 2002/0060649 A1 | 5/2002 | Perlman | |
| 2008/0151185 A1 | 6/2008 | Saito et al. | |
| 2010/0045571 A1 | 2/2010 | Yamamoto | |
| 2015/0062716 A1* | 3/2015 | Komatsu | G02B 27/0172 359/630 |

FOREIGN PATENT DOCUMENTS

| | | |
|---|---|---|
| JP | H07-311361 | 11/1995 |
| JP | H09163192 A | 6/1997 |
| JP | 2006-098820 | 4/2006 |
| JP | 2008-145701 | 6/2008 |
| WO | WO 2009/066446 | 5/2009 |

* cited by examiner

DISPLAY APPARATUS

CROSS REFERENCE TO RELATED APPLICATIONS

This application is a national stage application under 35 U.S.C. 371 and claims the benefit of PCT Application No. PCT/JP2019/008613 having an international filing date of 5 Mar. 2019, which designated the United States, which PCT application claimed the benefit of Japanese Patent Application No. 2018-056326 filed 23 Mar. 2018, the entire disclosures of each of which are incorporated herein by reference.

TECHNICAL FIELD

The present disclosure relates to a display apparatus.

BACKGROUND ART

A head-mounted image display apparatus mounted on an observer's head is known from, for example, Japanese Patent Application Laid-Open No. 2005-309264. The image display apparatus 1 disclosed in this patent publication includes a head mounting unit 6 mounted on an observer's head and a body carrying unit 7 carried by the observer's body. The head mounting unit 6 is provided with a convex lens 8 constituting a transfer optical system 5, and a part of an azimuth and distance detection system. The head mounting unit 6 includes a light emitting unit R including an infrared LED, an actuator 27 for moving the convex lens 8, and a drive circuit 28.

CITATION LIST

Patent Document

Patent Document 1: Japanese Patent Application Laid-Open No. 2005-309264

SUMMARY OF THE INVENTION

Problems to be Solved by the Invention

By the way, in the technique disclosed in the above-mentioned patent publication, the light emitting unit R provided in the head mounting unit 6, the actuator 27, and the drive circuit 28 require a power source (battery). Therefore, it is a structure in which a burden is imposed on the observer, such as an increase in the mass and size of the head mounting unit 6. In a case where it is assumed that the light emitting unit R, the actuator 27, and the drive circuit 28 are removed and only the convex lens 8 is mounted on the head mounting unit 6, when the observer moves, the positional relationship between the body carrying unit, the head mounting unit, and the pupil of the observer is broken, and a projected image deviates from the observer's pupil. As a result, a problem that it becomes difficult to observe the image occurs. Furthermore, in this image display apparatus, it is premised that the positions of the head mounting unit and the observer's pupil are properly aligned. However, in the practical use of the image display apparatus, due to the position error during initial adjustment, the change over time during use (misalignment of the head mounting unit 6), the position reproducibility when attaching and detaching the head mounting unit 6, and the like, it is difficult to always maintain the state of the positional relationship in which the head mounting unit 6 matches and the observer's pupil. Then, due to the above reasons, there arises a problem that the projected image does not surely reach the observer's pupil.

Therefore, an object of the present disclosure is to provide a display apparatus having a configuration and a structure that can surely make an image reach an observer's pupil without imposing a burden on the observer.

Solutions to Problems

A display apparatus according to a first aspect of the present disclosure for achieving the aforementioned object includes:

an eyepiece optical system; and an image display apparatus including an image forming apparatus and a transfer optical system that emits an image incident from the image forming apparatus to the eyepiece optical system, in which the eyepiece optical system and the image display apparatus are arranged to be spatially separated from each other, the eyepiece optical system forms an image from the transfer optical system on a retina of an observer, the image display apparatus further includes a first position detection apparatus that detects a position of the eyepiece optical system, a second position detection apparatus that detects a position of a pupil of the observer, and a transfer optical system controlling apparatus, and on the basis of positional information of the eyepiece optical system detected by the first position detection apparatus and positional information of the pupil of the observer detected by the second position detection apparatus, the transfer optical system controlling apparatus controls the transfer optical system such that the image incident from the image forming apparatus reaches the eyepiece optical system.

A display apparatus according to a second aspect of the present disclosure for achieving the aforementioned object includes:

an eyepiece optical system; and an image display apparatus including an image forming apparatus and a transfer optical system that emits an image incident from the image forming apparatus to the eyepiece optical system, in which the eyepiece optical system and the image display apparatus are arranged to be spatially separated from each other, the eyepiece optical system forms an image from the transfer optical system on a retina of an observer, the image display apparatus further includes a first position detection apparatus that detects a position of the eyepiece optical system, a second position detection apparatus that detects a position of a pupil of the observer, and a transfer optical system controlling apparatus, and the second position detection apparatus is arranged at a position where the pupil of the observer can be seen.

BRIEF DESCRIPTION OF DRAWINGS

FIG. 3C is a diagram for explaining an angle $\theta_1$ formed by a straight line connecting a center of the eyepiece optical system and a center of the observer's pupil and a normal line passing through the center of the eyepiece optical system, and an angle $\theta_2$ formed by a light beam emitted from a center of an image forming apparatus passing through the transfer optical system, and reaching the eyepiece optical system and a normal line passing through the center of the eyepiece optical system.

MODE FOR CARRYING OUT THE INVENTION

Figure 1A:
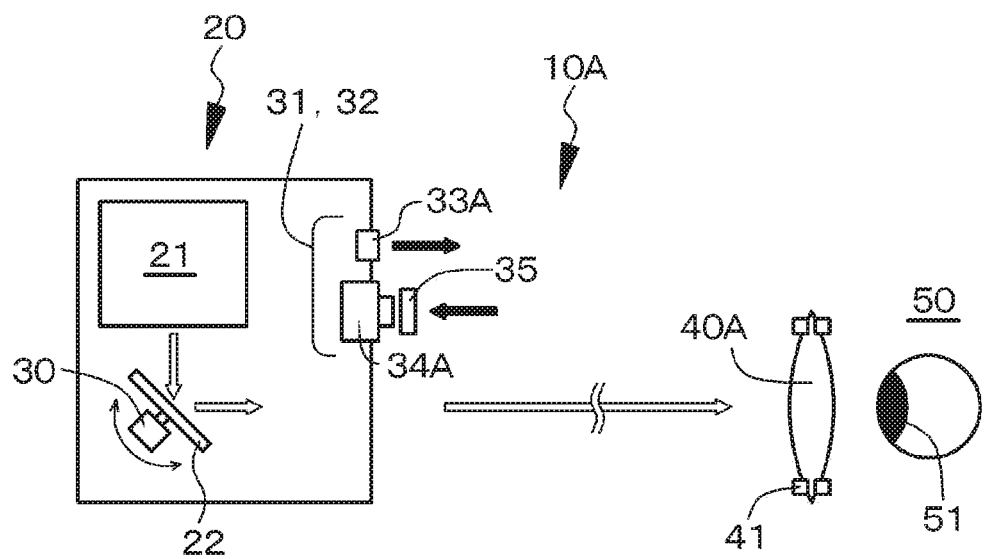
FIGS. 1A and 1B are respectively a conceptual diagram of a display apparatus of Example 1, and a diagram showing control of a transfer optical system and an image forming apparatus on the basis of an image acquired by a first position detection apparatus (positional information of a retroreflective marker) and an image acquired by a second position detection apparatus (positional information of an observer's pupil) in the display apparatus of Example 1.

Hereinafter, the present disclosure will be described on the basis of Examples with reference to the drawings, but the present disclosure is not limited to the Examples. Various numerical values and materials in the Examples are examples. Note that the description is provided in the order set forth below.

1. General description of display apparatus according to first aspect to second aspect of the present disclosure
2. Example 1 (display apparatus according to first aspect to second aspect of the present disclosure)
3. Example 2 (variation of Example 1)
4. Example 3 (another variation of Example 1)
5. Example 4 (variation of Examples 1 to 3)
6. Example 5 (variation of Example 3)
7. Example 6 (variation of Examples 1 to 5)
8. Example 7 (variation of Examples 1 to 6)
9. Example 8 (variation of Examples 1 to 7)
10. Other <Description of General Matters According to First Aspect to Second Aspect of the Present Disclosure>

In the display apparatus according to the first aspect of the present disclosure, on the basis of the positional information of the eyepiece optical system detected by the first position detection apparatus and the positional information of the observer's pupil detected by the second position detection apparatus, the transfer optical system controlling apparatus controls the transfer optical system so that the image incident from the image forming apparatus reaches the eyepiece optical system. However, it may be a form in which the transfer optical system is controlled so that all the images incident from the image forming apparatus reach the eyepiece optical system, or it may be a form in which the transfer optical system is controlled so that some of the images incident from the image forming apparatus reach the eyepiece optical system. The display apparatus according to the first aspect to the second aspect of the present disclosure is a retinal projection type display apparatus based on Maxwellian view. In the following description, the display apparatus according to the first aspect of the present disclosure and the display apparatus according to the second aspect of the present disclosure may be collectively referred to as the "display apparatus of the present disclosure".

In the display apparatus of the present disclosure including the preferable forms described above, the eyepiece optical system and the image display apparatus can be in a relatively movable form. That is, the image display apparatus is arranged at a position distant from the observer, or at a part of the observer distant from the observer's head. In the latter case, for example, although it is not limited, the image display apparatus is mounted as a wearable device at a site distant from the observer's head such as the observer's wrist. Alternatively, the image display apparatus is arranged in a personal computer, or is arranged in a state of being connected to the personal computer. Alternatively, the image display apparatus is provided in an external facility or the like, as described later.

Then, in the display apparatus of the present disclosure including the preferable forms described above, the eyepiece optical system can be in a form of being mounted on the observer, or alternatively, the eyepiece optical system can be in a form of being arranged at a position distant from the observer (that is, the eyepiece optical system is not mounted on the observer).

Furthermore, in the display apparatus of the present disclosure including the preferable forms described above, the transfer optical system may be in a form of including a movable mirror. When the horizontal direction (X-axis direction) and the vertical direction (Y-axis direction) are set with respect to the observer, examples of the movable mirror include, for example, a two-dimensionally rotatable mirror or micro electro mechanical systems (MEMS) mirror that moves an image incident from the image forming apparatus in the horizontal direction and the vertical direction. Alternatively, the movable mirror includes a movable mirror that is movable in three axes.

Furthermore, in the display apparatus of the present disclosure including the preferable forms described above, when the angle formed by the straight line connecting the center of the eyepiece optical system and the center of the observer's pupil and the normal line passing through the center of the eyepiece optical system is $\theta_1$, the angle formed by the light beam emitted from the center of the image forming apparatus passing through the transfer optical system, and reaching the eyepiece optical system and the normal line passing through the center of the eyepiece optical system is $\theta_2$, and the focal length of the eyepiece optical system is $f_0$ (unit: mm), the diameter of the observer's pupil strongly depends on the environment and the state of the observer, and is said to be 2 mm to 7 mm.

The transfer optical system controlling apparatus thus can be in a form of controlling the transfer optical system so as to satisfy $$f_0 \cdot |\tan(\theta_2) - \tan(\theta_1)| \leq 3.5,$$

preferably, $$f_0 \cdot |\tan(\theta_2) - \tan(\theta_1)| \leq 1,$$

more preferably $\theta_1 = \theta_2$.

Furthermore, in the display apparatus of the present disclosure including the preferable forms described above, the second position detection apparatus includes a light emitting unit that emits infrared light, and a light receiving unit that receives the infrared light reflected by the observer's pupil; and the eyepiece optical system can have a wavelength-dependent light-collecting characteristic, and in this case, it can be configured such that the infrared light emitted from the light emitting unit is not affected by the light-collecting characteristic of the eyepiece optical system. Then, in these cases, the eyepiece optical system can have a position display means (position detected means), specifically, a retroreflective marker attached thereto. Furthermore, in these cases, the eyepiece optical system can be configured by a hologram lens. The hologram lens can have a known configuration and structure. Note that it is preferable that the infrared light emitted from the light emitting unit be not affected by the light-collecting characteristic of the eyepiece optical system or be hardly affected by the light-collecting characteristic of the eyepiece optical system. That is, specifically, it is preferable that the infrared light emitted from the light emitting unit be not collected or be slightly collected by the hologram lens constituting the eyepiece optical system. The light emitting unit can be configured by, for example, a light emitting diode that emits infrared light or a combination of a semiconductor laser element that emits infrared light and a light diffusion plate, and the light receiving unit can be configured by an imaging apparatus (infrared camera) or a sensor (infrared sensor) that can detect infrared light. By mounting a filter (infrared transmission filter) that allows only the wavelength of infrared light used for detection to pass in front of the imaging apparatus, it is possible to simplify image processing in the subsequent stage.

Alternatively, in the display apparatus of the present disclosure including the preferable forms described above, the second position detection apparatus can include a light receiving unit that receives visible light reflected by the observer's pupil. Specifically, the light receiving unit receives visible light that is external light (environmental light) reflected by, for example, colliding with the observer's pupil. Then, in this case, the eyepiece optical system can have a wavelength-dependent light-collecting characteristic, and furthermore, the eyepiece optical system can have a lens member or can also have a hologram lens. Then, the second position detection apparatus can specify the position of the eyepiece optical system by performing image processing on the obtained image of the eyepiece optical system. Although the retroreflective marker is unnecessary, for example, by attaching a color marker to the eyepiece optical system, the image processing can be simplified. The light receiving unit can include an imaging apparatus or sensor capable of detecting visible light.

Alternatively, in the display apparatus of the present disclosure including the preferable forms described above, the second position detection apparatus includes a light emitting unit that emits infrared light, and a light receiving unit that receives the infrared light reflected by the observer's pupil; and the eyepiece optical system can have a wavelength-dependent diffraction characteristic. In this case, it can be configured such that the infrared light emitted from the light emitting unit is affected by the diffraction characteristic of the eyepiece optical system and the infrared light emitted from the light emitting unit is not affected by the light-collecting characteristic of the eyepiece optical system. Then, in these cases, the eyepiece optical system can include a diffractive optical member, and the diffractive optical member is not limited, but can include a diffractive member having a diffractive function and a light collecting member having a light collecting function. Here, the diffractive member may include a transmissive volume hologram diffraction grating, and the light collecting member may include a transmissive hologram lens.

Furthermore, in the display apparatus of the present disclosure including the preferable forms and configurations described above, the eyepiece optical system can be in a form of including a light collecting member on which an image from the transfer optical system is incident, and a deflection member that guides the light emitted from the light collecting member to the observer's pupil. The image from the transfer optical system is changed in propagation and transfer direction in the direction of the deflection member in the light collecting member. Then, the focal length $f_0$ of the eyepiece optical system can be extended with this configuration. The light collecting member and the deflection member are not limited, but are attached to a support member, or provided on the support member integrally with the support member. The light collecting member can include a transmissive hologram lens or a reflective hologram lens, and the deflection member can include a transmissive volume hologram diffraction grating or a reflective volume hologram diffraction grating. It is also possible to adopt a form in which light that is incident on the light collecting member and emitted from the light collecting member is totally reflected once or more within the support member and then incident on the deflection member. Note that the term "total reflection" means internal total reflection or total reflection inside the support member.

In a case where the support member includes a transparent plastic material, the plastic material may be polyethylene terephthalate, polyethylene naphthalate, polycarbonate, cellulose ester such as cellulose acetate, fluorine polymer such as polyvinylidene fluoride or a copolymer of polytetrafluoroethylene and hexafluoropropylene, polyether such as polyoxymethylene, polyolefin such as polyacetal, polystyrene, polyethylene, polypropylene, methylpentene polymer, polyimide such as polyamide imide or polyether imide, polyamide, polyether sulfone, polyphenylene sulfide, polyvinylidene fluoride, tetra acetyl cellulose, brominated phenoxy, polyarylate, polysulfone, or the like. In a case where the support member includes glass, examples of the glass include transparent glasses such as soda-lime glass and white plate glass.

Figure 13A:
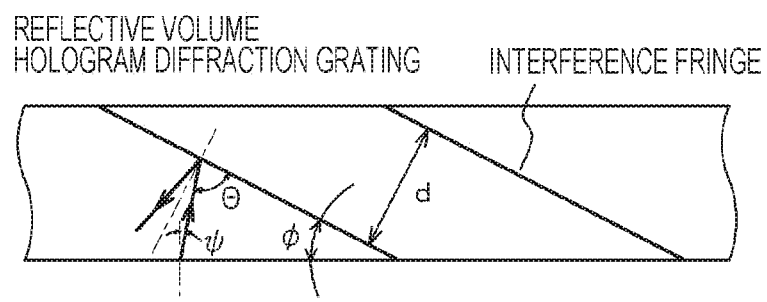
FIG. 13A is a schematic enlarged cross-sectional view showing a part of a reflective volume hologram diffraction grating.

FIG. 13A shows a schematic enlarged cross-sectional view showing a part of a reflective volume hologram diffraction grating. Interference fringes having an inclination angle (slant angle) φ are formed on the reflective volume hologram diffraction grating. The inclination angle φ refers to the angle formed by the interference fringes with the surface of the reflective volume hologram diffraction grating. The interference fringes are formed from the inside of the reflective volume hologram diffraction grating to the surface thereof. The interference fringes satisfy the Bragg condition. The Bragg condition means a condition that satisfies the following Formula (A). In Formula (A), m is a positive integer, λ is a wavelength, d is the pitch of a grating surface (distance in the normal direction of a virtual plane including interference fringes), and Θ is a complementary angle of the angle of incidence on the interference fringes. Furthermore, in a case where light enters the reflective volume hologram diffraction grating at incident angle ψ, the relationship between Θ, the inclination angle φ, and the incident angle ψ is as shown in Formula (B).

$$m \cdot \lambda = 2 \cdot d \cdot \sin(\Theta) \quad (A)$$

$$\Theta = 90° - (\varphi + \psi) \quad (B)$$

Figure 14:
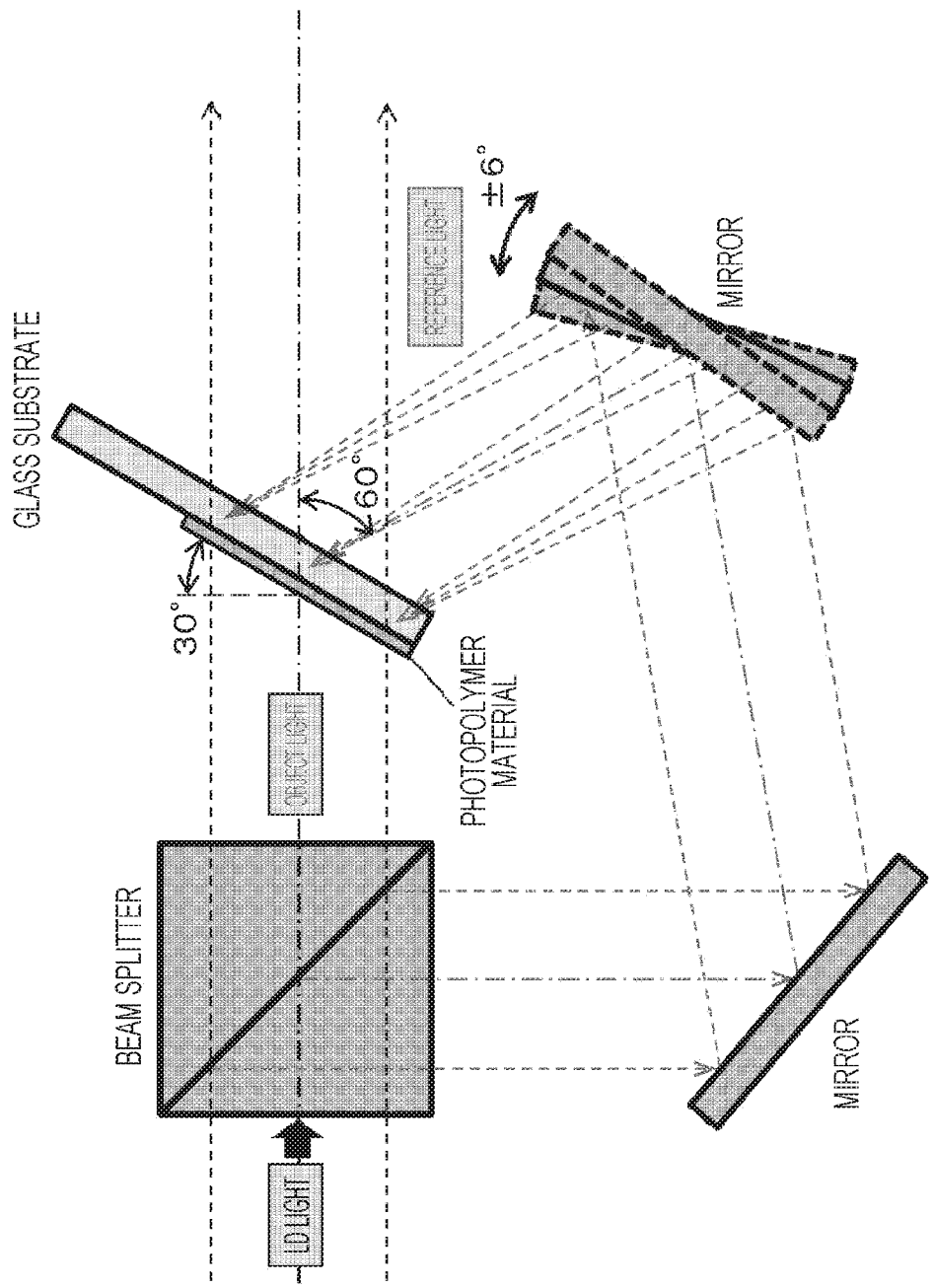
FIG. 14 is a diagram for explaining a method of manufacturing a reflective volume hologram diffraction grating.

A photopolymer material can be mentioned as a constituent material of the volume hologram diffraction grating. The constituent material and the basic structure of the volume hologram diffraction grating are only required to be the same as the constituent material and structure of a conventional volume hologram diffraction grating. Interference fringes are formed from the inside of the volume hologram diffraction grating to the surface thereof, and a method of forming such interference fringes themselves is only required to be the same as a conventional forming method. Specifically, as shown in FIG. 14, for example, it is sufficient if a member (for example, a photopolymer material) constituting the volume hologram diffraction grating is irradiated with object light from a first predetermined direction on one side and simultaneously the member constituting the volume hologram diffraction grating is irradiated with reference light from a second predetermined direction on the other side, such that the interference fringes formed by the object light and the reference light are recorded inside the volume hologram diffraction grating. In the example shown in FIG. 14, a mirror for irradiating the photopolymer material with the reference light is inclined by 60 degrees and (60±6 degrees), and the reference light is emitted to the photopolymer material three times in total. In the volume hologram diffraction grating thus obtained, the incident image can be divided into three images. By appropriately selecting the first predetermined direction, the second predetermined direction, the wavelengths of the object light and the reference light, a desired pitch of the interference fringes on the surface of the volume hologram diffraction grating and a desired inclination angle (slant angle) of the interference fringes can be obtained. The inclination angle of the interference fringe means the angle formed by the surface of the volume hologram diffraction grating and the interference fringe. In a case where the volume hologram diffraction grating includes a stack structure of volume hologram diffraction grating layers of P layer, it is sufficient if such stacking of volume hologram diffraction grating layers is manufactured such that volume hologram diffraction grating layers of P layer are separately manufactured, and then the volume hologram diffraction grating layers of P layer are stacked (adhered) using, for example, an ultraviolet curable adhesive. Furthermore, the volume hologram diffraction grating layer of P layer may be manufactured as follows. A volume hologram diffraction grating layer of one layer using a photopolymer material having an adhesive property is manufactured and then the photopolymer material having an adhesive property is sequentially bonded onto the layer to manufacture a volume hologram diffraction grating layer. Such a volume hologram diffraction grating is of a refractive index modulation type. By irradiating the manufactured volume hologram diffraction grating layer with energy rays as necessary, the monomers in the photopolymer material remaining without being polymerized when the volume hologram diffraction grating layer is irradiated with the object light and the reference light may be polymerized and fixed. If necessary, heat treatment may be performed for stabilization.

Furthermore, in the display apparatus of the present disclosure including the preferable forms and configurations described above, the first position detection apparatus may be in a form of emitting and receiving infrared light, but is not limited to this, and may be in a form of receiving visible light having a predetermined wavelength. Note that, in the former case, the light emitting unit constituting the first position detection apparatus can include, for example, a light emitting diode that emits infrared light or a combination of a semiconductor laser element that emits infrared light and a light diffusion plate, and the light receiving unit constituting the first position detection apparatus can include an imaging apparatus (infrared camera) or a sensor (infrared sensor) that can detect infrared light. By mounting a filter (infrared transmission filter) that allows only the wavelength of infrared light used for detection to pass in front of the imaging apparatus, it is possible to simplify image processing in the subsequent stage. On the other hand, in the latter case, the light receiving unit can include an imaging apparatus or sensor capable of detecting visible light. Furthermore, the light emitting unit and the light receiving unit constituting the first position detection apparatus may be in a form of being common (shared) with the light emitting unit and the light receiving unit constituting the second position detection apparatus.

Furthermore, the display apparatus of the present disclosure including the preferable forms and configurations described above can be in a form in which, on the basis of the positional information of the eyepiece optical system detected by the first position detection apparatus and the positional information of the observer's pupil detected by the second position detection apparatus, the position of the image formed in the image forming apparatus is corrected.

Furthermore, in the display apparatus of the present disclosure including the preferable forms and configurations described above, the eyepiece optical system may be in a form of including a diffraction grating. The diffraction grating is an optical element that causes a diffraction phenomenon by a grating pattern. A plurality of images is obtained on the basis of the kth-order diffraction light emitted from the diffraction grating (however, k=0, ±1, ±2 . . . ). Note that when an image including parallel light is incident on the diffraction grating, the light rays constituting each of the images emitted from the diffraction grating also become parallel light.

The diffraction grating can include, but is not limited to, a transmissive diffraction grating or a transmissive hologram diffraction grating (specifically, a transmissive volume hologram diffraction grating), or a reflective diffraction grating or a reflective hologram diffraction grating (specifically, a reflective volume hologram diffraction grating). In a case where the diffraction grating includes a transmissive diffraction grating or a transmissive hologram diffraction grating, when the incident angle ψ of the light constituting the image is constant, in order to obtain the plurality of images divided by the diffraction grating and emitted from the diffraction grating, it is necessary to change the value of Θ in various ways. To change the value of Θ, it is sufficient if the value of the inclination angle φ is changed from Formula (B) and furthermore the value of the pitch d of the grating surface is changed from Formula (A). In other words, by appropriately selecting the value of the inclination angle φ and the value of the pitch d of the grating surface, the image incident on the diffraction grating including the volume hologram diffraction grating can be divided by the diffraction grating, and a plurality of images can be emitted from the diffraction grating.

Figure 13B:
FIGS. 13B and 13C are a reflective blazed diffraction grating and a schematic partially cross-sectional view of a reflective blazed diffraction grating having a step shape (however, hatching lines are omitted).
Figure 13C:
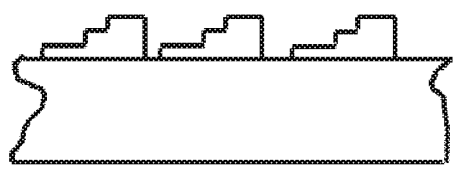

Alternatively, the diffraction grating may have a well-known configuration and structure, and examples include a reflective blazed diffraction grating (see FIG. 13B) and a reflective blazed diffraction grating having a step shape (see FIG. 13C). However, the diffraction grating is not limited to these diffraction gratings. The grating pattern is configured such that, for example, linear recesses and protrusions are arranged in parallel at a cycle of a micrometer size, and the cycle, the pattern thickness (difference between recess and protrusion), or the like is appropriately selected on the basis of the wavelength range of light emitted from the image forming apparatus. The diffraction grating can be manufactured by a known method.

It is possible to adopt a form in which an image can be divided into at least two images by the diffraction grating provided in the eyepiece optical system. Specifically, for example, it is possible to exemplify a form in which the diffraction grating divides the image into three images in the horizontal direction, a form in which the diffraction grating divides the image into three images in the vertical direction, a form in which the diffraction grating divides the image into three images in the horizontal direction and three images in the vertical direction into a cross (form in which one image including the center light path overlaps and the image is divided into five images in total), a form in which the diffraction grating divides the image into two images in the horizontal direction and two images in the vertical direction, 2×2=4, and a form in which the diffraction grating divides the image into three images in the horizontal direction and three images in the vertical direction, 3×3=9.

In the display apparatus of the present disclosure including the preferable forms and configurations described above, the eyepiece optical system can be of a semi-transmissive (see-through) type, which allows the outside scene to be viewed through the eyepiece optical system. Then, in this case, the eyepiece optical system can be in a form of including a hologram lens or being provided with a hologram lens. In some cases, the eyepiece optical system may be a non-transmissive type (a form in which the outside scene cannot be viewed through the eyepiece optical system).

In the display apparatus of the present disclosure including the various preferable forms and configurations described above, the image display apparatus may be in a form of being arranged in front of the observer. Note that the image display apparatus, as long as it is arranged in front of the observer, although depending on the specifications of the transfer optical system and the eyepiece optical system, may be located higher than the observer's head, may be located at the same level as the observer's head, may be located lower than the observer's head, may be located facing the observer, or may be located at an angle to the observer. In a case where the display apparatus is a non-transmissive type, the image display apparatus can be arranged in front of the observer.

In the display apparatus of the present disclosure including the various preferable forms and configurations described above, the image forming apparatus may be in a form of having a plurality pixels arranged in a two-dimensional matrix. Such a configuration of the image forming apparatus is referred to as a "first configuration image forming apparatus" for the sake of convenience.

Examples of the first configuration image forming apparatus include an image forming apparatus including a reflective spatial light modulation apparatus and a light source; an image forming apparatus including a transmissive spatial light modulation apparatus and a light source; and an image forming apparatus including a light emitting element such as organic electro luminescence (EL), an inorganic EL, a light emitting diode (LED), a semiconductor laser element. Among them, an image forming apparatus including an organic EL light emitting element (organic EL display apparatus), and an image forming apparatus including a reflective spatial light modulation apparatus and a light source are preferable. Examples of the spatial light modulation apparatus include a light valve, for example, a transmissive or reflective liquid crystal display apparatus such as liquid crystal on silicon (LCOS), a digital micromirror device (DMD), and examples of the light source include a light emitting element. Moreover, the reflective spatial light modulation apparatus includes a liquid crystal display apparatus, and a polarization beam splitter that reflects a part of the light from the light source and guides it to the liquid crystal display apparatus, and passes a part of the light reflected by the liquid crystal display apparatus and guides it to the transfer optical system. Examples of the light emitting element constituting the light source include a red light emitting element, a green light emitting element, a blue light emitting element, and a white light emitting element. Alternatively, white light may be obtained by mixing the red light, the green light, and the blue light emitted respectively from the red light emitting element, the green light emitting element, and the blue light emitting element using a light pipe to uniformize the brightness. Examples of the light emitting element include a semiconductor laser element, a solid-state laser, and an LED. It is sufficient if the number of pixels is determined on the basis of the specifications required for the image forming apparatus, and specific values of the number of pixels include 320×240, 432×240, 640×480, 1024×768, 1920×1080, or the like. In the first configuration image forming apparatus, the diaphragm may be in a form of being arranged at the front focal point (focal point on the image forming apparatus side) of a lens system (described later).

Alternatively, the image forming apparatus of the display apparatus of the present disclosure including the preferable forms and configurations described above may be in a form of including a light source and a scanning means that scans light emitted from the light source to form an image. Such an image forming apparatus is referred to as a "second configuration image forming apparatus" for the sake of convenience.

The light source of the second configuration image forming apparatus can include a light emitting element, specifically, a red light emitting element, a green light emitting element, a blue light emitting element, and a white light emitting element. Alternatively, white light may be obtained by mixing the red light, the green light, and the blue light emitted respectively from the red light emitting element, the green light emitting element, and the blue light emitting element with a light pipe to uniformize the brightness. Examples of the light emitting element include a semiconductor laser element, a solid-state laser, and an LED. It is sufficient if the number of pixels (virtual pixels) in the second configuration image forming apparatus is also determined on the basis of the specifications required for the image forming apparatus, and specific values of the number of pixels (virtual pixels) include 320×240, 432×240, 640×480, 1024×768, 1920×1080, or the like. Furthermore, in the case of displaying a color image and in a case where the light source includes a red light emitting element, a green light emitting element, and a blue light emitting element, it is preferable to perform color combination using, for example, a cross prism. The scanning means can include, for example, a MEMS mirror or a galvano mirror having a two-dimensionally rotatable micromirror that horizontally and vertically scans the light emitted from the light source. In the second configuration image forming apparatus, the MEMS mirror or the galvano mirror may be in a form of being arranged at the front focal point (focal point on the image forming apparatus side) of a lens system (described later).

In the first configuration image forming apparatus or the second configuration image forming apparatus, the light that has become a plurality of parallel light beams by a lens system (an optical system that turns emitted light into parallel light) is made to incident on the transfer optical system (specifically, for example, a movable mirror). In order to generate parallel light, specifically, as described above, for example, it is sufficient if the light emitting unit of the image forming apparatus is positioned at the location (position) of the focal length in the lens system. As the lens system, an optical system having a positive optical power as a whole including a convex lens, a concave lens, a free-form surface prism, and a hologram lens may be used alone or in combination can be exemplified. Between the lens system and the transfer optical system, a light shielding unit having an opening may be arranged in the vicinity of the lens system so that undesired light is not emitted from the lens system or incident on the transfer optical system.

In the display apparatus of the present disclosure, the eyepiece optical system may be in a form of being attached to the frame. The frame includes a front portion arranged in front of the observer, two temple portions rotatably attached to both ends of the front portion via hinges, and a nose pad. A tip portion is attached to the end of each temple portion. Furthermore, the front portion and the two temple portions can be integrally configured. The assembly of the frame (including the rim portion) and the nose pad has substantially the same structure as ordinary eyeglasses. The material constituting the frame including the nose pad can include the same material as that constituting ordinary eyeglasses, such as metal, alloy, plastic, or a combination thereof. Alternatively, the eyepiece optical system can be in a form of being attached to goggles or in a form of being formed integrally with the goggles, or may be in a form of being attached to a surface member (face member, mask member) having a shape similar to a disaster prevention face that can be mounted on the observer's head or in a form of being integrally formed with the surface member.

The eyepiece optical system mounted on the observer has a very simple structure and does not require a battery or the like for driving because it does not have a drive unit, and the eyepiece optical system can be easily reduced in size and weight. Unlike conventional HMDs, the image display apparatus is not mounted on the observer's head. As described above, the image display apparatus is arranged in an external facility or the like, or is mounted on the observer's wrist or the like as a wearable device. Examples in which the image display apparatus is arranged in an external facility or the like include:

(A) An example in which an image display apparatus for passengers is attached to the back surface of a back (backrest) of the seat of a vehicle or aircraft (B) An example in which an image display apparatus for audience is attached to the back surface of the back (backrest) of a seat in a theater or the like (C) An example in which an image display apparatus for drivers and the like is attached to vehicles, aircraft, automobiles, motorcycles, bicycles, or the like (D) An example of being used as an alternative to monitors used in personal computers, mobile phones, smart watches, or the like (E) An example of being used as an alternative to a display or touch panel used in an automated teller machine at a financial institution (F) An example of being used as an alternative to a display or touch panel used in stores and offices (G) An example of enlarging and displaying the screen of a mobile phone or personal computer (H) An example of being used as an alternative to a display plate and the like used in museums, amusement parks, or the like (I) An example in which an image display apparatus for customers is attached to tables such as of coffee shops and cafes In the display apparatus of the present disclosure including various preferable forms and configurations described above, a signal for displaying an image in the image forming apparatus (a signal for forming a virtual image in the eyepiece optical system) can be in a form of being received from the outside (outside the system of the display apparatus). In such a form, information and data associated with an image displayed on the image forming apparatus are recorded, stored, and saved in, for example, a so-called cloud computer or server. As the image display apparatus includes a communication means, such as a telephone line, an optical line, a mobile phone, a smartphone, or by combining an image display apparatus and communication means, it is possible to transfer or exchange various information and data between the cloud computer or server and the image display apparatus. Further, a signal based on various information and data, i.e., a signal for displaying an image in the image forming apparatus can be received. Alternatively, the signal for displaying an image in the image forming apparatus may be in a form of being stored in the image display apparatus. The image displayed on the image forming apparatus includes various information and various data. The image display apparatus, which is a wearable device, can also be in a form of including a camera (imaging apparatus), and the image captured by the camera may be sent to the cloud computer or server via the communication means, and various information and data corresponding to the image captured by the camera may be searched in the cloud computer or server, the various information and data searched may be sent to the image display apparatus via the communication means, and the various information and data searched may be displayed as the image in the image forming apparatus.

The display apparatus of the present disclosure including the various forms and configurations described above can be used for, for example, display of various information and the like on various sites on the Internet; display of various explanations of operation, manipulation, maintenance, disassembly and the like of observation objects such as various apparatuses and symbols, signs, marks, emblems, designs, and the like; display of various explanations about observation targets such as people and articles and symbols, signs, marks, emblems, designs, and the like; display of moving images or still images; display of subtitles of movies or the like; display of explanations and closed captions related to pictures synchronized with the pictures; various explanations about observation targets in plays, Kabuki, Noh, Kyogen, opera, music concerts, ballet, various plays, amusement grounds (amusement parks), museums, tourist spots, tourist resorts, tourist guides, and the like, and display of explanations or the like for explaining the contents, progress, background, and the like, and display of closed captions. In plays, Kabuki, Noh, Kyogen, opera, concerts, ballet, various plays, amusement grounds (museum parks), museums, tourist spots, tourist resorts, tourist guides, and the like, it is sufficient if characters as images related to observation targets are displayed on the image forming apparatus at an appropriate timing. Specifically, for example, according to the progress status of a movie or the like or according to the progress status of a play or the like, on the basis of a predetermined schedule and time allocation, by an operator's operation or under the control of a computer or the like, an image control signal is sent to the image forming apparatus, and the image is displayed on the image forming apparatus. Furthermore, display of various explanations about various apparatuses, people, articles, and the like is performed, but the image forming apparatus can perform display of various explanations about observation targets such as the various apparatuses, people, and articles, which are preliminarily formed by taking (capturing) the observation targets such as the various apparatuses, people, and articles with a camera and analyzing the taken (captured) content with the image forming apparatus.

Example 1

Example 1 relates to the display apparatus of the present disclosure

As shown in the conceptual diagram of FIG. 1A, a display apparatus 10A of Example 1, if described according to the first aspect of the present disclosure, includes an eyepiece optical system 40A, and an image display apparatus 20 including an image forming apparatus 21 and a transfer optical system 22 that emits an image incident from the image forming apparatus 21 to the eyepiece optical system 40A. Then, the eyepiece optical system 40A and the image display apparatus 20 are arranged to be spatially separated from each other, and the eyepiece optical system 40A forms an image from the transfer optical system 22 on the retina of an observer 50. The image display apparatus 20 further includes a first position detection apparatus 31 that detects the position of the eyepiece optical system 40A, a second position detection apparatus 32 that detects the position of a pupil 51 of the observer 50, and a transfer optical system controlling apparatus 30, in which on the basis of the positional information of the eyepiece optical system 40A detected by the first position detection apparatus 31 and the positional information of the pupil 51 of the observer 50 detected by the second position detection apparatus 32, the transfer optical system controlling apparatus 30 controls the transfer optical system 22 such that the image incident from the image forming apparatus 21 reaches the eyepiece optical system 40A, that is, the image incident from the image forming apparatus 21 is formed on the retina of the observer 50 via the eyepiece optical system 40A.

Furthermore, a display apparatus 10A of Example 1, if described according to the second aspect of the present disclosure, includes an eyepiece optical system 40A, and an image display apparatus 20 including an image forming apparatus 21 and a transfer optical system 22 that emits an image incident from the image forming apparatus 21 to the eyepiece optical system 40A. Then, the eyepiece optical system 40A and the image display apparatus 20 are arranged to be spatially separated from each other, and the eyepiece optical system 40A forms an image from the transfer optical system 22 on the retina of an observer 50. The image display apparatus 20 further includes a first position detection apparatus 31 that detects the position of the eyepiece optical system 40A, a second position detection apparatus 32 that detects the position of a pupil 51 of the observer 50, and a transfer optical system controlling apparatus 30, in which the second position detection apparatus 32 is arranged at a position where the pupil 51 of the observer 50 can be seen.

The display apparatus of Example 1 is a retinal projection type display apparatus based on Maxwellian view. Then, in the display apparatus 10A of Example 1, the eyepiece optical system 40A and the image display apparatus 20 are relatively movable. That is, the image display apparatus 20 is arranged at a position away from the observer 50. The eyepiece optical system 40A is mounted on the observer 50 (specifically, on the head of the observer 50). Moreover, the transfer optical system 22 includes a movable mirror. Specifically, when the horizontal direction (X-axis direction) and the vertical direction (Y-axis direction) are set with respect to the observer 50, examples of the movable mirror 22 include, for example, a two-dimensionally rotatable mirror or micro electro mechanical systems (MEMS) mirror that moves an image incident from the image forming apparatus 21 in the horizontal direction and the vertical direction. The movable mirror 22 includes a movable mirror that is movable in three axes.

Here, as described above, it is important that the positional relationship between the second position detection apparatus 32, the eyepiece optical system 40A, and the pupil 51 of the observer 50 has a positional relationship in which the pupil 51 of the observer 50 can be detected from the second position detection apparatus 32. Furthermore, it is also important to give the second position detection apparatus 32 an optical characteristic so that the pupil 51 of the observer 50 can be detected from the second position detection apparatus 32.

In the display apparatus 10A of Example 1, the second position detection apparatus 32 includes a light emitting unit 33A that emits infrared light and a light receiving unit 34A that receives the infrared light reflected by the pupil 51 of the observer 50. Then, the eyepiece optical system 40A has the wavelength-dependent light-collecting characteristic, and further, the infrared light emitted from the light emitting unit 33A is not affected by the light-collecting characteristic of the eyepiece optical system 40A. The eyepiece optical system 40A includes, but is not limited to, a hologram lens. A position display means, specifically, a retroreflective marker 41 is attached to the eyepiece optical system 40A. The retroreflective marker 41 is a light-reflecting component manufactured so that the incident light and the reflected light are in the same direction, and by utilizing this characteristic, in principle, even if the observer 50 makes a large movement, the reflected light always returns to the first position detection apparatus 31. As a result, the position of the retroreflective marker 41 can be detected regardless of the relative positional relationship between the first position detection apparatus 31 and the retroreflective marker 41. The retroreflective marker 41 is desirably camouflage color with respect to a frame 52.

The eyepiece optical system 40A collects visible light emitted from the image forming apparatus 21 to form an image on the retina of the observer 50, while infrared light emitted from the light emitting unit 33A will not be collected by the eyepiece optical system 40A. The infrared light emitted from the light emitting unit 33A does not interfere with the image and has a wavelength band in which the pupil 51 of the observer 50 has a high reflectance. The eyepiece optical system 40A is attached to a rim portion of the frame 52 (shown only in FIGS. 12A and 12B described later) having a structure substantially the same as that of ordinary eyeglasses. The frame 52 includes a front portion arranged in front of the observer 50, two temple portions rotatably attached to both ends of the front portion via hinges, and a nose pad. A tip portion is attached to the end of each temple portion. The assembly of the frame (including the rim portion) 52 and the nose pad can have a well-known configuration and structure.

In the display apparatus 10A of Example 1, the first position detection apparatus 31 emits infrared light. Specifically, the first position detection apparatus 31 includes a light emitting unit that emits infrared light and a light receiving unit that detects the return light from the eyepiece optical system 40A. Here, the light emitting unit and the light receiving unit constituting the first position detection apparatus 31 are common (shared) with the light emitting unit 33A and the light receiving unit 34A constituting the second position detection apparatus 32.

The light emitting unit 33A includes, for example, a light emitting diode that emits infrared light or a combination of a semiconductor laser element that emits infrared light and a light diffusion plate, and the light receiving unit 34A includes an imaging apparatus (infrared camera) or a sensor (infrared sensor) that can detect infrared light. By mounting a filter (infrared transmission filter) 35 that allows only the wavelength of infrared light used for detection to pass in front of the imaging apparatus, it is possible to simplify image processing in the subsequent stage. The light emitting unit 33A illuminates the entire head of the observer 50. The infrared light emitted from the light emitting unit 33A collides with the retroreflective marker 41 attached to the eyepiece optical system 40A, and is returned to the light receiving unit 34A so that the position of the eyepiece optical system 40A can be detected and specified. Furthermore, the infrared light emitted from the light emitting unit 33A passes through the eyepiece optical system 40A, illuminates the pupil 51 of the observer 50, is reflected by the pupil 51 of the observer 50, passes through the eyepiece optical system 40A, and is returned to the light receiving unit 34A such that the position of the pupil 51 of the observer 50 can be detected and specified. That is, the second position detection apparatus 32 is arranged at a position where the pupil 51 of the observer 50 can be seen. Here, specifically, in Example 1, in order to reduce the mounting burden of the eyepiece optical system 40A imposed on the observer 50, the light emitting unit 33A and the light receiving unit 34A are mounted on the image display apparatus 20. Then, the light receiving unit 34A is arranged so that the position of the pupil 51 of the observer 50 can be detected by the light receiving unit 34A (imaging apparatus, infrared camera) or sensor (infrared sensor). In some cases, the light emitting unit 33A may be separated from the image display apparatus 20 and arranged in a place different from the image display apparatus 20, or the light receiving unit 34A may be separated from the image display apparatus 20 and arranged in a place different from the image display apparatus 20. However, it is important that the light receiving unit 34A is arranged at a position where the pupil 51 of the observer 50 can be seen (that is, directly seen or indirectly seen) regardless of the form. Note that, in FIG. 1A, the infrared light emitted from the light emitting unit 33A and the infrared light returning to the light receiving unit 34A are indicated by black arrows, and the luminous flux of visible light (image) emitted from the transfer optical system (movable mirror) 22 is indicated by blank arrows.

Figure 2A:
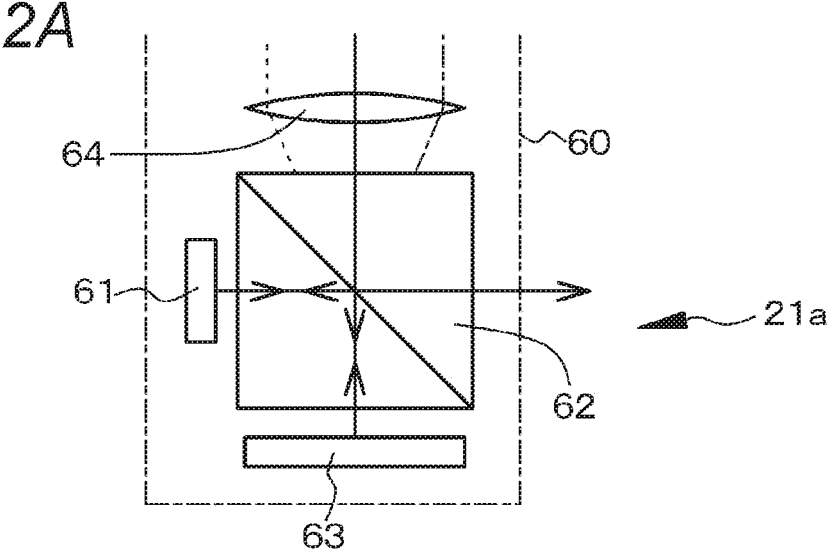
FIGS. 2A, 2B, and 2C are conceptual diagrams of the image forming apparatus in the display apparatus of Example 1.

As shown in FIG. 2A, the image forming apparatus 21 (hereinafter, the image forming apparatus shown in FIG. 2A is referred to as an image forming apparatus 21a) is the first configuration image forming apparatus, and has a plurality of pixels arranged in a two-dimensional matrix. Specifically, the image forming apparatus 21a includes a reflective spatial light modulation apparatus and a light source 61 including a light emitting diode that emits white light. Each image forming apparatus 21a is entirely housed in a housing 60 (indicated by the chain line in FIG. 2A), and an opening (not shown) is formed in the housing 60, and light is emitted from an optical system (parallel light emitting optical system, collimating optical system 64) via the opening. The housing 60 is attached to the image display apparatus 20 by a suitable means. The reflective spatial light modulation apparatus includes a liquid crystal display apparatus (LCD) 63 including LCOS as a light valve. Moreover, a polarization beam splitter 62 that reflects a part of the light from the light source 61 and guides it to the liquid crystal display apparatus 63, and passes a part of the light reflected by the liquid crystal display apparatus 63 and guides it to the optical system 64 is provided. The liquid crystal display apparatus 63 includes a plurality of (for example, 640×480) pixels (liquid crystal cells, liquid crystal display elements) arranged in a two-dimensional matrix. The polarization beam splitter 62 has a well-known configuration and structure. The non-polarized light emitted from the light source 61 collides with the polarization beam splitter 62. In the polarization beam splitter 62, a P-polarized component passes and is emitted to the outside of the system. On the other hand, an S-polarized component is reflected by the polarization beam splitter 62, incident on the liquid crystal display apparatus 63, reflected inside the liquid crystal display apparatus 63, and is emitted from the liquid crystal display apparatus 63. Here, within the light emitted from the liquid crystal display apparatus 63, the light emitted from the pixel displaying "white" contains a large amount of P-polarized component, and the light emitted from the pixel displaying "black" contains a large amount of S-polarized component. Therefore, within the light emitted from the liquid crystal display apparatus 63 and colliding with the polarization beam splitter 62, the P-polarized component passes through the polarization beam splitter 62 and is guided to the optical system 64. On the other hand, the S-polarized component is reflected by the polarization beam splitter 62 and returned to the light source 61. The optical system 64 includes, for example, a convex lens, and in order to generate parallel light, the image forming apparatus 21a (more specifically, the liquid crystal display apparatus 63) is arranged at the location (position) of the focal length in the optical system 64. The image emitted from the image forming apparatus 21a reaches the retina of the observer 50 via the transfer optical system 22 and the eyepiece optical system 40A.

Figure 2B:
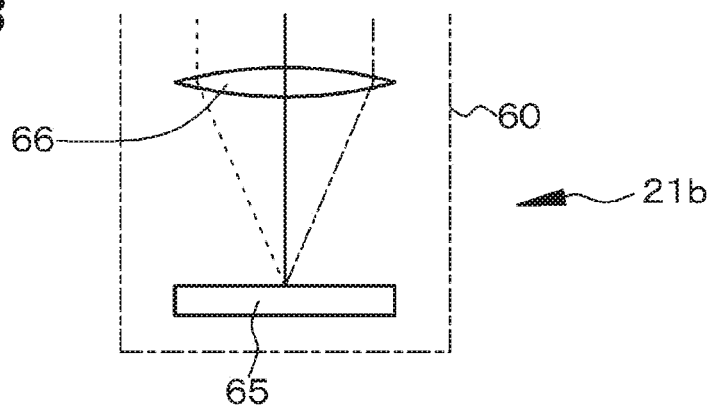

Alternatively, as shown in FIG. 2B, an image forming apparatus 21 (hereinafter, the image forming apparatus shown in FIG. 2B is referred to as an image forming apparatus 21b) includes an organic EL display apparatus 65. The image emitted from the organic EL display apparatus 65 passes through a convex lens 66, becomes parallel light, and reaches the retina of the observer 50 via the transfer optical system 22 and the eyepiece optical system 40A. The organic EL display apparatus 65 includes a plurality of (for example, 640×480) pixels (organic EL elements) arranged in a two-dimensional matrix.

Figure 2C:
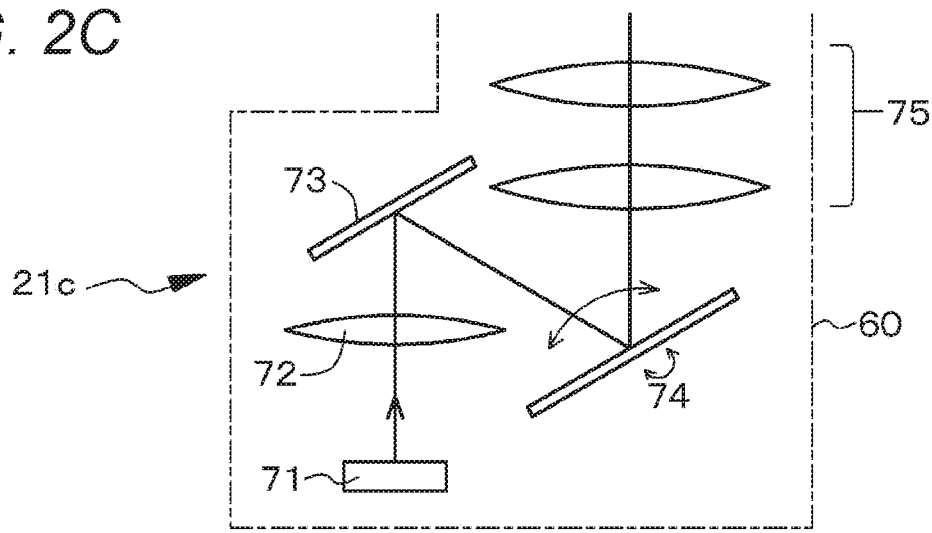

Alternatively, as shown in FIG. 2C, the image forming apparatus 21, which is the second configuration image forming apparatus, (hereinafter, the image forming apparatus shown in FIG. 2C is referred to as an image forming apparatus 21c) includes a light source 71, a collimating optical system 72 that turns the light emitted from the light source 71 into parallel light, a scanning means 74 that scans the parallel light emitted from the collimating optical system 72, and a relay optical system 75 that relays and emits the parallel light scanned by the scanning means 74. Note that the image forming apparatus 21c is entirely housed in a housing 60 (indicated by the chain line in FIG. 2C), and an opening (not shown) is formed in the housing 60, and light is emitted from the relay optical system 75 via the opening. Then, the housing 60 is attached to the image display apparatus 20 by a suitable means. The light source 71 includes a light emitting element, specifically, a light emitting diode or a semiconductor laser element. Then, the light emitted from the light source 71 is incident on the collimating optical system 72 having a positive optical power as a whole, and is emitted as parallel light. Then, the parallel light is reflected by the total reflection mirror 73, subjected to horizontal scanning and vertical scanning by the scanning means 74 including MEMS, having a two-dimensionally rotatable micro mirror, and capable of two-dimensionally scanning the incident parallel light, turned into a type of two-dimensional image, to generate virtual pixels (for example, the number of pixels can be the same as that of the image forming apparatus 21a). Then, the light from the virtual pixels passes through the relay optical system (parallel light emitting optical system) 75 including a well-known relay optical system, and the image emitted from the image forming apparatus 21c reaches the retina of the observer 50 via the transfer optical system 22 and the eyepiece optical system 40A. When the light source 71 includes a red light emitting element, a green light emitting element, and a blue light emitting element, the observer 50 can detect a color image, and when the light source 71 includes one kind of light emitting element, the observer 50 can detect a monochrome image.

As described above, the image generated by the image forming apparatus 21 is incident on the transfer optical system (specifically, the movable mirror) 22 in the state of parallel light (or almost parallel light), reflected by the transfer optical system 22, and then converted into a luminous flux which is directed to the eyepiece optical system 40A. The eyepiece optical system 40A is arranged such that the pupil 51 of the observer 50 is located at the position of the focal point (focal length $f_0$) of the eyepiece optical system 40A, and the projected luminous flux is condensed by the eyepiece optical system 40A and passes through the pupil of the observer 50 so as to be directly drawn on the retina, and the observer 50 can recognize the image.

At this time, the position of the eyepiece optical system 40A is detected by the first position detection apparatus 31, and the position of the pupil 51 of the observer 50 is detected by the second position detection apparatus 32. Then, on the basis of these two detection results, the transfer optical system controlling apparatus 30 controls the inclination of the transfer optical system (specifically, the movable mirror) 22 such that even if the positional relationship between the eyepiece optical system 40A and the pupil 51 of the observer 50 changes, the image is formed on the retina of the observer 50. The transfer optical system controlling apparatus 30 has a well-known configuration and structure.

Figure 1B:
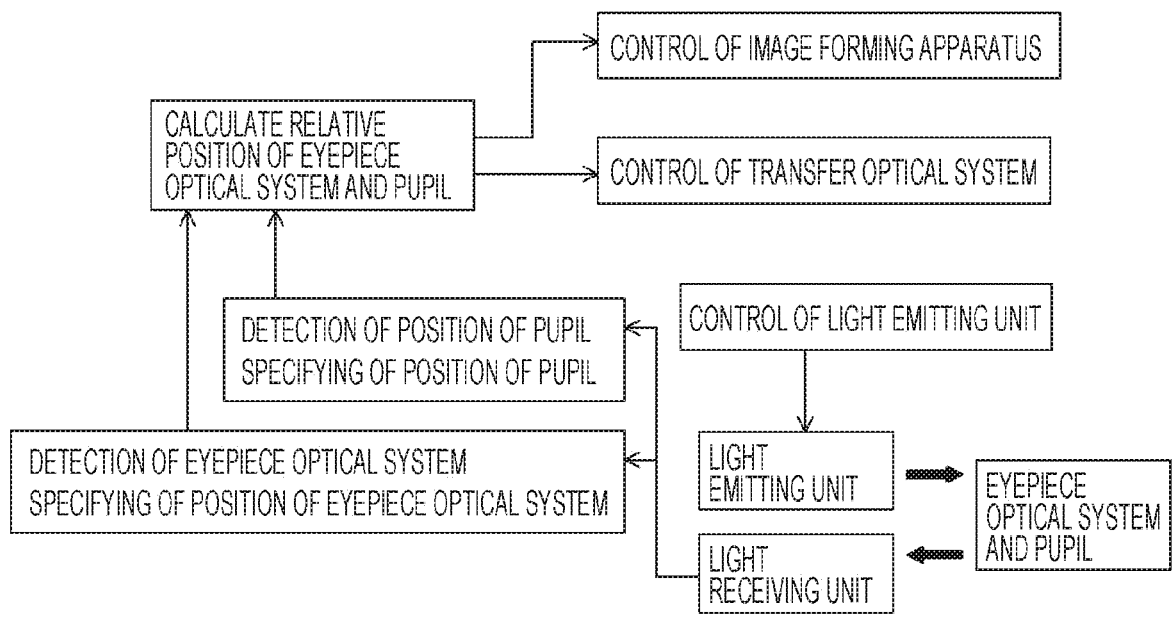

On the basis of the image acquired by the first position detection apparatus 31 (positional information of the retroreflective marker 41) and the image acquired by the second position detection apparatus 32 (positional information of the pupil 51 of the observer 50), the control of the transfer optical system (specifically, movable mirror) 22 and the image forming apparatus 21 is shown in FIG. 1B.

That is, first, the light emitting unit 33A constituting the first position detection apparatus 31 and the second position detection apparatus 32 irradiates the vicinity of the head of the observer 50 with infrared light. Then, an image including the infrared light reflected by the retroreflective marker 41 and the pupil 51 of the observer 50 is taken by the light receiving unit (infrared camera) 34A.

Then, the obtained signal and noise are sorted on the basis of a method such as pattern recognition or shape recognition, the position of the retroreflective marker 41 is detected and specified, and the position of the pupil 51 of the observer 50 is detected and specified. The method of detecting the pupil position is widely known as a line-of-sight detection technique, and it can be obtained from the center of gravity of a reflection area or the boundary of a differential image by utilizing the fact that the infrared light reflectance of the pupil 51 is high. A drive circuit (not shown) of the light emitting unit 33A may be provided with a modulation function (specifically, for example, pulsed infrared light is emitted from the light emitting unit 33A) and used for image recognition.

In this way, the position of the eyepiece optical system 40A is detected and specified by the first position detection apparatus 31, while the position of the pupil 51 of the observer 50 is detected and specified by the second position detection apparatus 32. Either of these may be performed first or these may be performed simultaneously.

Then, the relative relationship between the position of the eyepiece optical system 40A and the position of the pupil 51 of the observer 50 is calculated. Since it is assumed that the distance from the eyepiece optical system 40A to the pupil 51 of the observer 50 matches the focal length $f_0$ of the eyepiece optical system 40A, from the calculation result of the relative relationship between the position of the eyepiece optical system 40A and the position of the pupil 51 of the observer 50, an angle (for the sake of convenience, referred to as the "projection angle") θ1 formed by a straight line $L_1$ connecting the center of the eyepiece optical system 40A and the center of the pupil 51 of the observer 50 and a normal line $L_{NL}$ passing through the center of the eyepiece optical system 40A can be obtained. Then, on the basis of the calculation result, a control signal is sent to the transfer optical system controlling apparatus 30, the inclination of the movable mirror 22 is changed, and the direction of the light (for the sake of convenience, referred to as the "projection light") emitted from the transfer optical system 22 (movable mirror) is changed so that the image can be made to reach the pupil 51 of the observer 50.

The distance between the eyepiece optical system 40A and the pupil 51 of the observer 50 can be obtained from the relative size of the retroreflective marker 41 and the pupil 51 reflected in the light receiving unit 34A constituting the first position detection apparatus 31 and the second position detection apparatus 32. Note that, when the image formed by the image forming apparatus 21 is controlled (for example, when a lens is arranged on the image emission side of the transfer optical system 22 and the distance between the transfer optical system 22 and the lens is controlled), the projection light can be appropriately diverged and converged (can be non-parallel light), and the image can be formed on the retina of the observer 50 even in a case where the distance between the eyepiece optical system 40A and the pupil 51 of the observer 50 changes. Furthermore, the distance from the transfer optical system 22 to the eyepiece optical system 40A (referred to as "projection distance $L_0$" for the sake of convenience) is not necessarily needed to obtain the angle $\theta_2$, but it can be used for correction or calculation of the limit of misalignment in a case where the positional relationship between the transfer optical system 22, the eyepiece optical system 40A, and the pupil 51 of the observer 50 largely deviates. The projection distance $L_0$ can be obtained by calibrating the distance between a plurality of retroreflective markers 41 and the size of the retroreflective marker 41, can be obtained by using a distance sensor such as a time of flight (TOF) sensor, or can be indirectly obtained by subtracting the distance between the eyepiece optical system 40A and the pupil 51 of the observer 50 from the distance between the transfer optical system 22 and the pupil 51 of the observer 50. The light receiving unit 34A may not be shared by the first position detection apparatus 31 and the second position detection apparatus 32, but a light receiving unit dedicated to the first position detection apparatus 31 and a light receiving unit dedicated to the second position detection apparatus 32 may be provided. Similarly, the light emitting unit 33A may not be shared by the first position detection apparatus 31 and the second position detection apparatus 32, but a light emitting unit dedicated to the first position detection apparatus 31 and a light emitting unit dedicated to the second position detection apparatus 32 may be provided.

In a case where an image is observed with one eye, it is sufficient if one display apparatus 10A is used. Furthermore, in a case where an image is observed with both eyes, it is sufficient if two display apparatuses 10A are used, or one display apparatus having the following configuration may be used. That is, it may be a structure including two eyepiece optical systems, and an image display apparatus having one image forming apparatus and two transfer optical systems that divides an image incident from the one image forming apparatus and emits the images to the two eyepiece optical systems, or alternatively, it may be a structure including two eyepiece optical systems and an image display apparatus having one image forming apparatus and one transfer optical system onto which an image incident from the one image forming apparatus is incident and divided into two images, which are emitted to the two eyepiece optical systems.

Next, position control of the transfer optical system 22 will be described.

Figure 3A:
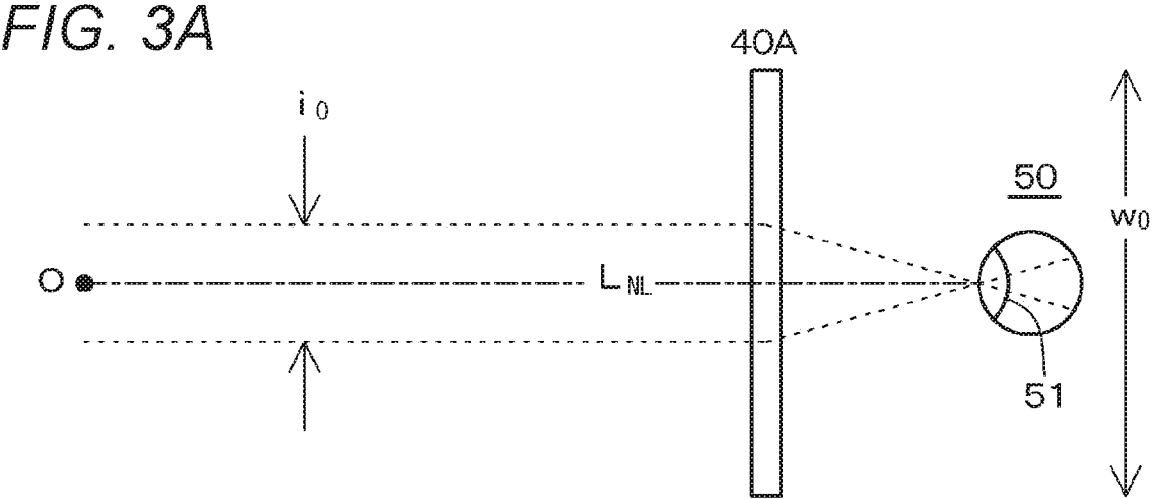
FIGS. 3A, 3B and 3C are diagrams schematically showing behavior of a luminous flux emitted from the transfer optical system, and a positional relationship between an eyepiece optical system and an observer's pupil, and particularly.
Figure 3B:
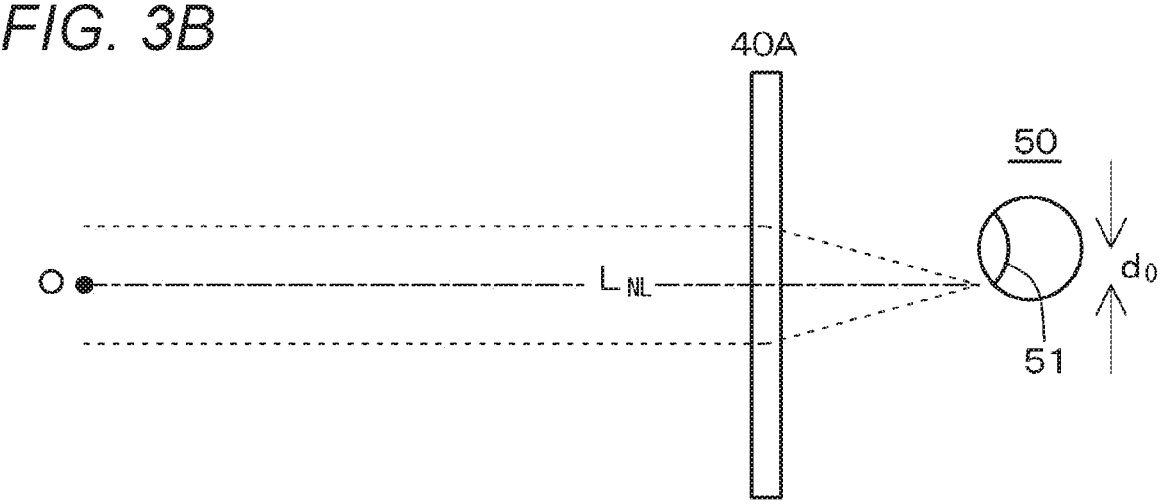
Figure 3C:
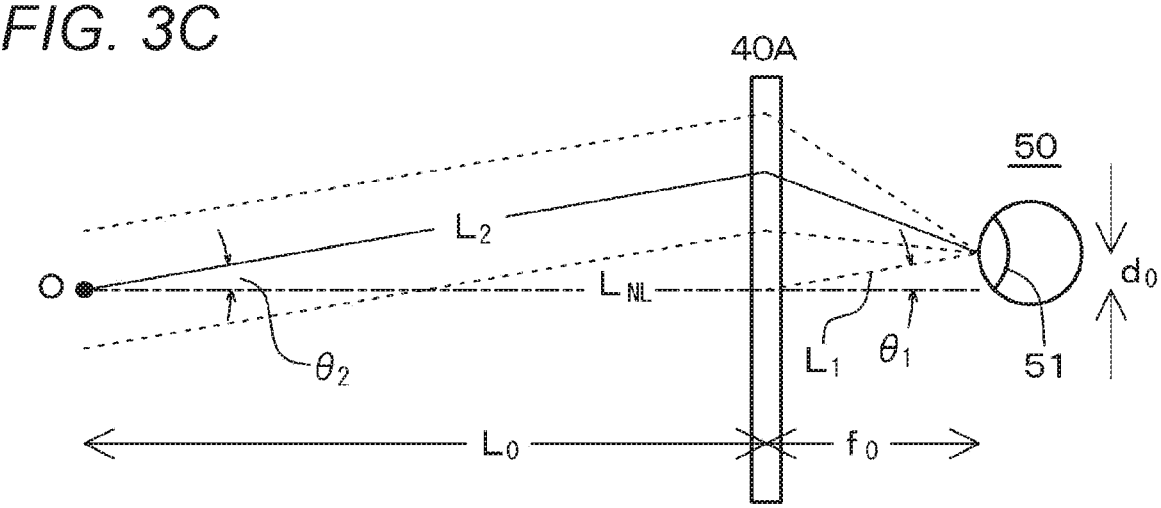

The behavior of the luminous flux emitted from the transfer optical system 22 and the positional relationship between the eyepiece optical system 40A and the pupil 51 of the observer 50 are schematically shown in FIGS. 3A, 3B, 3C, 4A and 4B. FIG. 3A shows a case where the positional relationship between the eyepiece optical system 40A and the pupil 51 of the observer 50 is in a normal state. FIG. 3B shows a case where the misalignment amount of the pupil 51 of the observer 50 with respect to the eyepiece optical system 40A becomes do. FIG. 3C shows a state in which the inclination of the movable mirror 22 is controlled and an image emitted from the movable mirror 22 is formed on the retina of the observer 50 in the state shown in FIG. 3B. In FIG. 3A and the like, "O" indicates the rotation center of the movable mirror 22, and a light beam emitted from the center of the image forming apparatus 21 collides with the rotation center "O" of the movable mirror 22. Furthermore, in FIGS. 3A, 3B, 3C, 4A, and 4B, a light beam emitted from the center of the image forming apparatus 21 is indicated by the thin solid lines, and a light beam corresponding to the outer edge of the image is indicated by the thin broken lines.

First, an ideal state in which the eyepiece optical system 40A is sufficiently large with respect to the relative misalignment between the center position of the eyepiece optical system 40A and the center position of the pupil 51 of the observer 50 will be described. In this case, when the angle formed by the straight line $L_1$ connecting the center of the eyepiece optical system 40A and the center of the pupil 51 of the observer 50 and the normal line $L_{NL}$ passing through the center of the eyepiece optical system 40A is $\theta_1$ (projection angle $\theta_1$), the angle formed by the light beam $L_2$ emitted from the center of the image forming apparatus 21 passing through the transfer optical system 22, and reaching the eyepiece optical system 40A and the normal line $L_{NL}$ passing through the center of the eyepiece optical system 40A is $\theta_2$, and the focal length of the eyepiece optical system is $f_0$ (unit: mm), it is sufficient if the transfer optical system controlling apparatus 30 controls the transfer optical system 22 so as to satisfy $$f_0 \cdot |\tan(\theta_2) - \tan(\theta_1)| \leq 3.5,$$

preferably, $$f_0 \cdot |\tan(\theta_2) - \tan(\theta_1)| \leq 1,$$

more preferably $\theta_1 = \theta_2$. Specifically, it is sufficient if the inclination of the movable mirror 22 is controlled. Note that, in the following, for the sake of simplification, description will be given on the basis of an example in which the transfer optical system controlling apparatus 30 controls the transfer optical system 22 so as to satisfy $\theta_1 = \theta_2$.

The angle $\theta_2$ can be obtained from Formula (1) as shown in FIG. 3C.

$$\theta_1 = \theta_2 = \tan^{-1}(d_0/f_0) \qquad (1)$$

where, $d_0$ . . . relative misalignment amount of an image (misalignment amount of the observer's pupil with respect to the eyepiece optical system).

On the other hand, assuming an actual display apparatus, the size of the eyepiece optical system 40A is finite. Therefore, when the movable mirror 22 is controlled so as to satisfy Formula (1), the state in which the image emitted from the image forming apparatus 21 does not reach the eyepiece optical system 40A, and the image does not reach the pupil 51 of the observer 50 can occur. Therefore, it is necessary to add the condition that Formula (1) is satisfied within the range in which the eyepiece optical system 40A spatially exists. Here, two assumptions are assumed for the state in which the image cannot be observed by the observer 50.

Figure 4A:
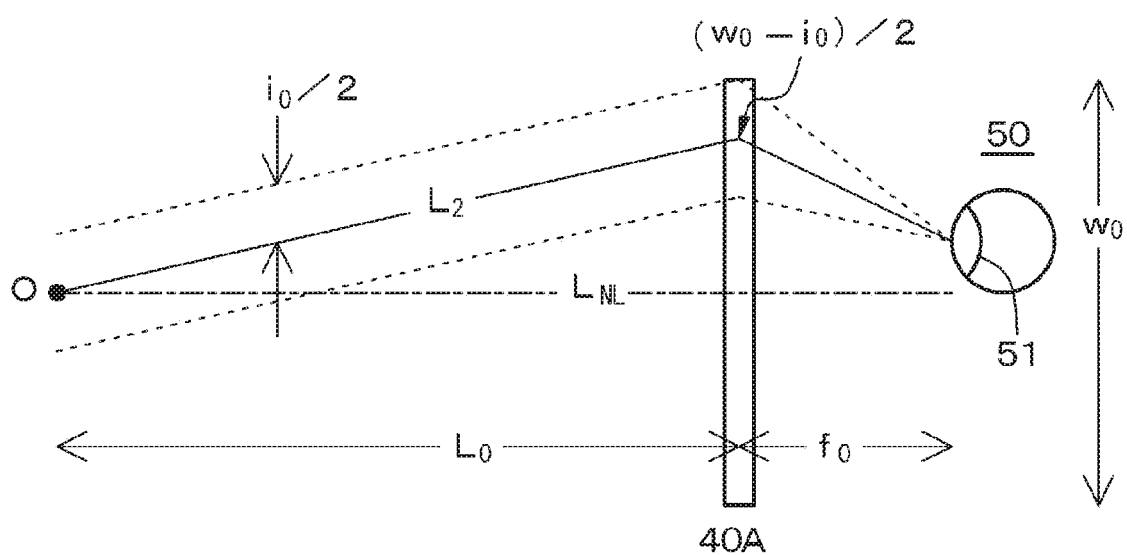
FIGS. 4A and 4B are a diagram schematically showing behavior of a luminous flux emitted from the transfer optical system, and a positional relationship between an eyepiece optical system and an observer's pupil, and a diagram for explaining an angle $\theta_1$ formed by a straight line connecting a center of the eyepiece optical system and a center of the observer's pupil and a normal line passing through the center of the eyepiece optical system, and an angle $\theta_2$ formed by a light beam emitted from a center of an image forming apparatus passing through the transfer optical system, and reaching the eyepiece optical system and a normal line passing through the center of the eyepiece optical system.

That is, the first assumption is that a part of the image should not be missing. As shown in FIG. 4A, the condition in the case where the image observed by the observer 50 is not allowed to be missing is as shown in Formula (2) below. Then, when Formula (2) is modified, Formula (3) is obtained. The state shown in FIG. 4A shows a state in which the outer edge of the outer side of the image emitted from the transfer optical system 22 reaches the outer edge of the eyepiece optical system 40A, showing a state in which if the image emitted from the transfer optical system 22 further moves upward in FIG. 4A, a part of the image will be missing.

$$|L_0 \cdot \tan(\theta_2)| \leq (w_0 - i_0)/2 \quad (2)$$

$$|L_0 \cdot (d_0/f_0)| \leq (w_0 - i_0)/2 \quad (3)$$

where,
$L_0$ ... projection distance
$w_0$ ... size of eyepiece optical system
$i_0$ ... length (size) of one side of projected image.

Within the range of Formula (3), it is sufficient if the movable mirror 22 is controlled so as to satisfy Formula (1) (the above-mentioned ideal condition). Furthermore, outside of this range, it is necessary to control the movable mirror 22 so that the luminous flux is projected inside the outer edge of the eyepiece optical system 40A. To summary, Formulae (4-1) and (4-2) are obtained.

In the case of $|L_0 \cdot (d_0/f_0)| \leq (w_0 - i_0)/2$ $$\theta_2 = \tan^{-1}(d_0/f_0) \quad (4-1)$$

In the case of $|L_0 \cdot (d_0/f_0)| > (w_0 - i_0)/2$ $$\theta_2 = \tan^{-1}\{(w_0 - i_0)/2L_0\} \quad (4-2)$$

Figure 4B:
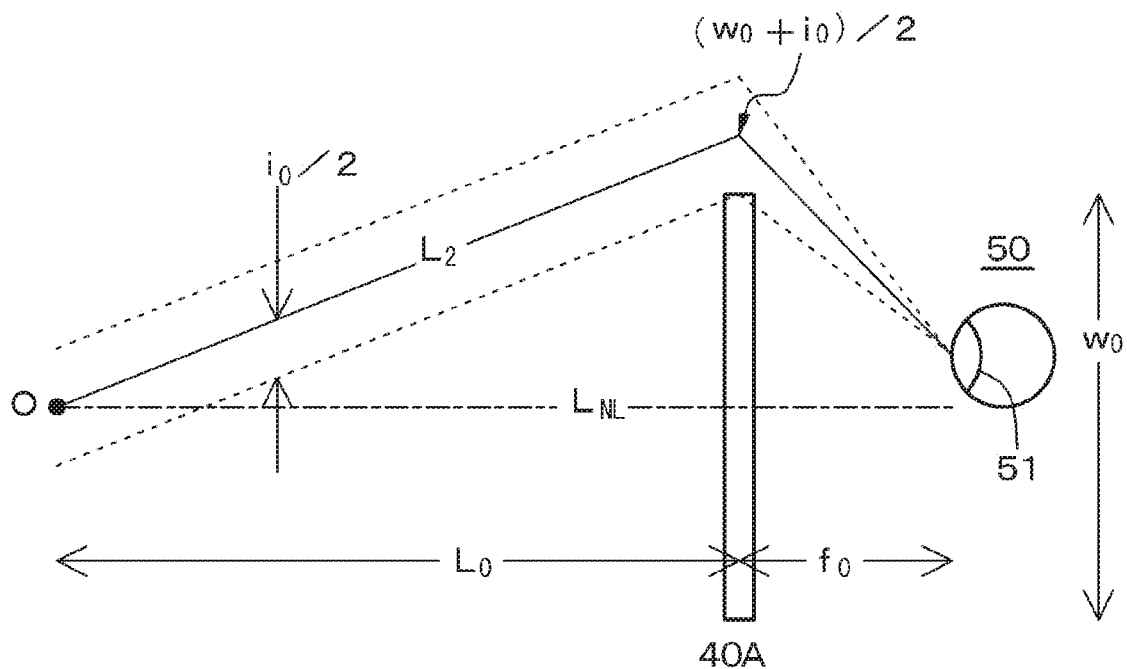

Furthermore, the second assumption is that a part of the image may be missing. The condition in the case where the image observed by the observer 50 is allowed to be missing is as shown in Formula (5) below. Then, when Formula (5) is modified, Formula (6) is obtained. Note that the state shown in FIG. 4B shows a state in which the outer edge of the inner side of the image emitted from the transfer optical system 22 reaches the outer edge of the eyepiece optical system 40A, showing a state in which if the image emitted from the transfer optical system 22 further moves upward in FIG. 4A, the image will be missing entirely.

$$|L_0 \cdot \tan(\theta_2)| \leq (w_0 + i_0)/2 \quad (5)$$

$$|L_0 \cdot (d_0/f_0)| \leq (w_0 + i_0)/2 \quad (6)$$

Outside of this range, it is sufficient if the movable mirror 22 is controlled so that the luminous flux overlaps even partially with the outer edge of the eyepiece optical system 40A. To summary, Formulae (7-1) and (7-2) are obtained. Note that $\theta_{limit}$ is the maximum value that $\theta_2$ (or the projection angle $\theta_1$) can take. Then, the range that $\theta_{limit}$ can take is $$\tan^{-1}\{(w_0 - i_0)/2L_0\} < \theta_{limit} < \tan^{-1}\{(w_0 + i_0)/2L_0\}.$$

In the case of $\theta_1 \leq \theta_{limit}$ $$\theta_2 = \tan^{-1}(d_0/f_0) \quad (7-1)$$

In the case of $\theta_1 > \theta_{limit}$ $$\theta_2 = \theta_{limit} \quad (7-2)$$

It is sufficient if the maximum value $\theta_{limit}$ of $\theta_2$ (or the projection angle $\theta_1$) is determined depending on how much missing of the image is allowed, and furthermore, the maximum value $\theta_{limit}$ of $\theta_2$ (or the projection angle $\theta_1$) varies according to the content of the image. For example, in the case of an image with a black background, it is preferable that the length (size) $i_0$ of one side of a projected image be set to be small.

The contents shown in Formulae (4-1), (4-2), (7-1), and (7-2) indicate that it is needed to perform projection with restrictions on $\theta_2$ (or projection angle $\theta_1$). Therefore, when the position of the pupil 51 of the observer 50 displaces and the value of the misalignment amount do increases, the observer 50 will eventually be unable to observe the image. It is necessary to consider the size of the pupil of the observer 50 as the condition that the image cannot be observed, and therefore, it also changes depending on the environment (brightness or the like). However, applying the present disclosure is equivalent to improving the robustness regarding the positional relationship with which the observer 50 can observe the image, and is very useful for more easily observing the image.

Then, in the display apparatus of Example 1, the image display apparatus arranged to be spatially separated from the eyepiece optical system includes the first position detection apparatus and the second position detection apparatus, and the transfer optical system controlling apparatus provided in the image display apparatus controls the transfer optical system, or alternatively, the second position detection apparatus is arranged at a position where the observer's pupil can be seen. Therefore, a power supply (battery) is not needed, and it is not a structure that imposes a burden on the observer, such as an increase in the mass and size of the eyepiece optical system, and the image can be reliably made to reach the pupil of the observer without imposing a burden on the observer.

Example 2

Figure 5A:
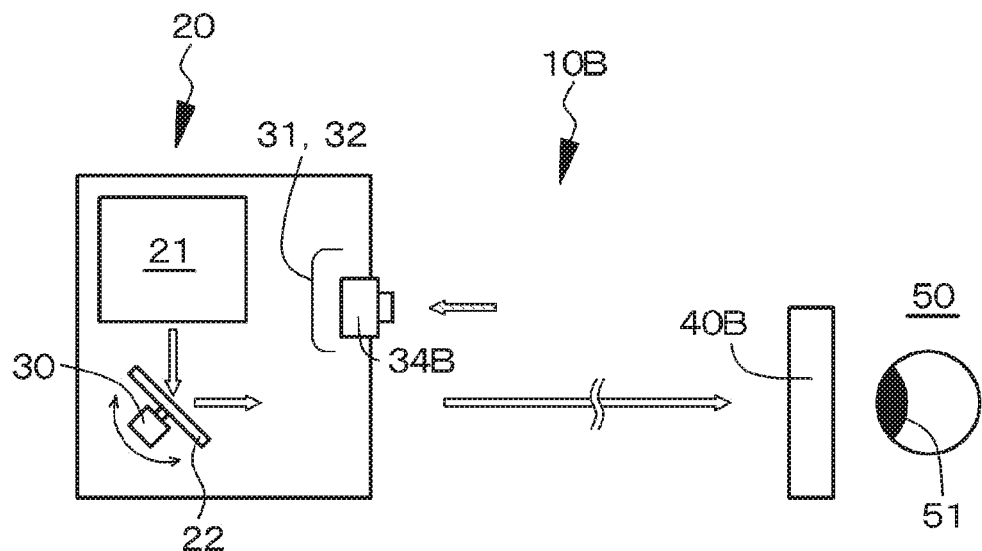
FIGS. 5A and 5B are conceptual diagrams of a display apparatus of Example 2 and a variation example thereof.
Figure 5B:
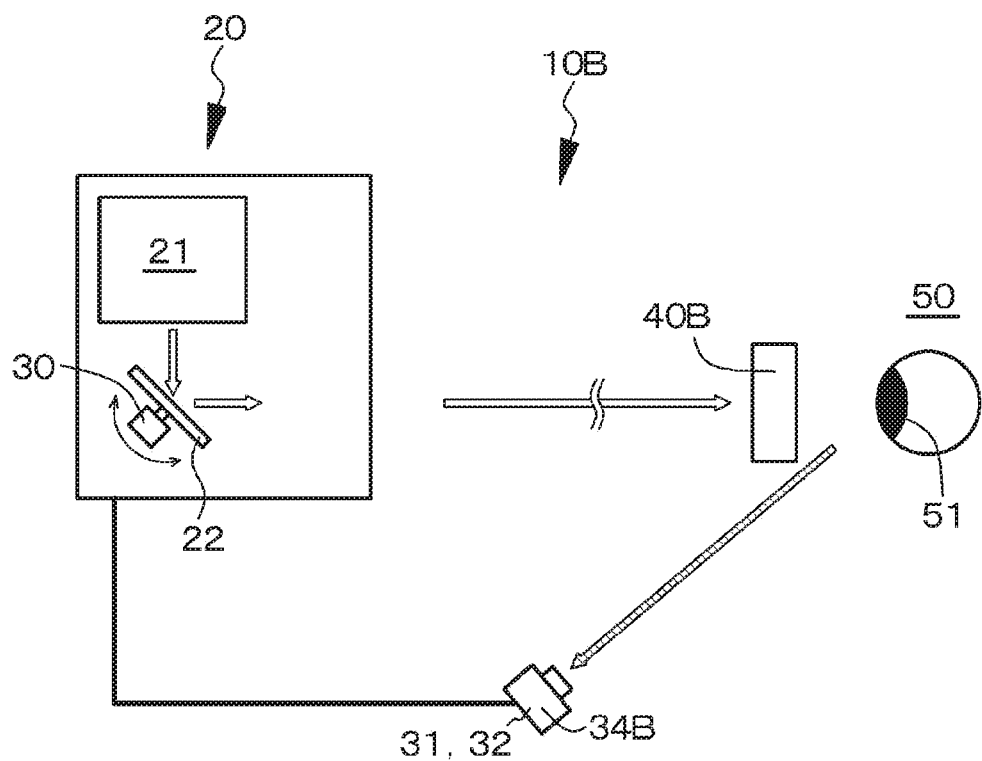

Example 2 is a variation of Example 1. A conceptual diagram of a display apparatus 10B of Example 2 is shown in FIG. 5A. In the display apparatus 10B of Example 2, a second position detection apparatus 32 includes a light receiving unit 34B that receives visible light (detection light) reflected by the pupil 51 of the observer 50. Specifically, the light receiving unit 34B receives visible light that is external light (environmental light) reflected by, for example, colliding with the pupil 51 of the observer 50. Then, an eyepiece optical system 40B has a wavelength-dependent light-collecting characteristic. Here, the eyepiece optical system 40B includes a lens member having a well-known configuration and structure or includes a hologram lens having a well-known configuration and structure. The eyepiece optical system 40B collects the image (visible light) emitted from the image forming apparatus 21 to form an image on the retina of the observer 50, while the visible light (detection light) is received by the light receiving unit 34B via the eyepiece optical system 40B. That is, similarly in Example 2, the second position detection apparatus 32 is arranged at a position where the pupil 51 of the observer 50 can be seen. Note that, in FIGS. 5A and 5B, the detection light returning to the light receiving unit 34B is shown by blank arrows with a hatching line, and the luminous flux of the visible light (image) emitted from the transfer optical system (movable mirror) 22 is shown by blank arrows. In the example shown in FIG. 5B, the second position detection apparatus 32 (light receiving unit 34B) is arranged at a position where the pupil 51 of the observer 50 can be seen directly (without the eyepiece optical system 40B).

In the display apparatus 10B of Example 2, the first position detection apparatus 31 includes a light receiving unit that detects the reflected light (detection light) from the eyepiece optical system 40B. Here, the light receiving unit constituting the first position detection apparatus 31 is common (shared) with the light receiving unit 34B constituting the second position detection apparatus 32. It is sufficient if the light receiving unit 34B includes an imaging apparatus (camera) or sensor that captures an image on the basis of visible light. Although the retroreflective marker is unnecessary, for example, by attaching a color marker to the eyepiece optical system 40B, the image processing can be simplified.

The first position detection apparatus 31 and the second position detection apparatus 32 (or part of them) may be attached as attachments to equipment such as smartphones, tablet type personal computers, or notebook type personal computers, and a camera built in the equipment can be used as the light receiving unit 34B. That is, as shown in the conceptual diagram of FIG. 5B, the first position detection apparatus 31 and the second position detection apparatus 32 do not necessarily have to be incorporated in the image display apparatus. Alternatively, the light receiving unit 34B may be arranged separately from the image display apparatus 20.

Example 3

Example 3 is also a variation example of Example 1. In a case where superimposition of an image and the background is required, it is desirable that the image display apparatus 20 be not located in front of the observer 50. In a case where the image display apparatus 20 always enters the field of view of the observer, the observer 50 may not be able to immerse himself/herself in the image or the outside scene. In a display apparatus 10C of Example 3, the image display apparatus 20 is arranged at a position other than the front of the observer 50. As a result, the observer 50 can observe the image and the outside scene while the image display apparatus 20 is not in the observer's field of view. That is, the display apparatus 10C can be of a semi-transmissive (see-through) type, and the outside scene can be viewed through the eyepiece optical system 40. However, when the image display apparatus 20 (specifically, the transfer optical system 22) is arranged at a position other than the front of the observer 50, the projection light is obliquely incident on the eyepiece optical system 40, resulting in a possibility that the focal point of the eyepiece optical system 40 deviates from the pupil 51 of the observer 50 and the image does reach the pupil 51 of the observer 50.

Figure 6:
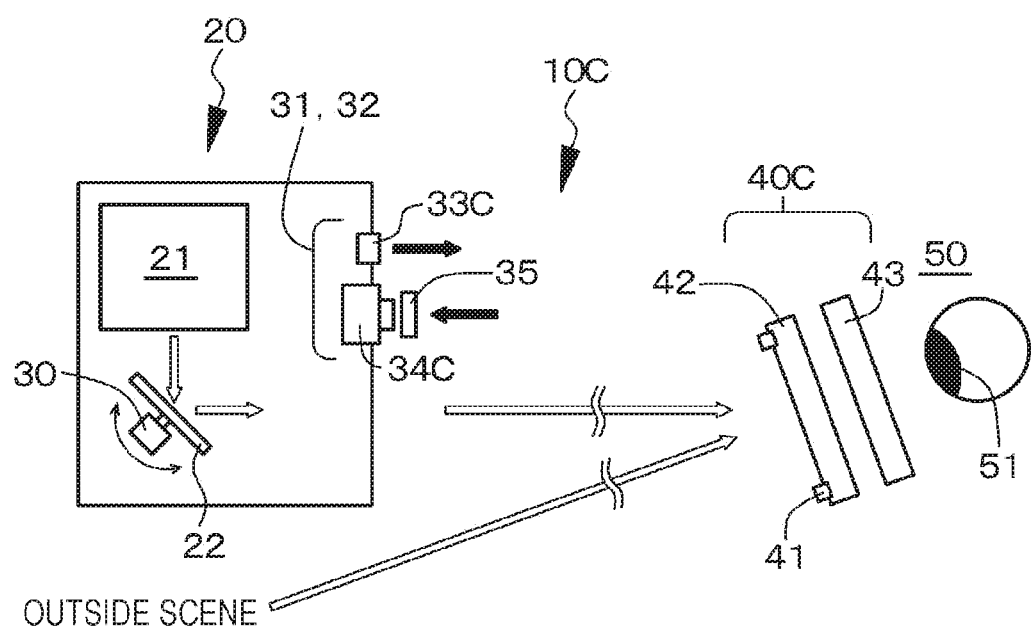
FIG. 6 is a conceptual diagram of a display apparatus of Example 3.

In order to deal with such a problem, as shown in a conceptual diagram in FIG. 6, the second position detection apparatus 32 includes a light emitting unit 33C that emits infrared light and a light receiving unit 34C that receives the infrared light reflected by the pupil 51 of the observer 50, and the eyepiece optical system 40C has a wavelength-dependent diffraction characteristic. Moreover, the infrared light emitted from the light emitting unit 33C is affected by the diffraction characteristic of the eyepiece optical system 40C, while the infrared light emitted from the light emitting unit 33C is not affected by the light-collecting characteristic of the eyepiece optical system 40. Furthermore, in the display apparatus 10C of Example 3, the eyepiece optical system 40C includes a diffractive optical member. Then, the eyepiece optical system 40C (diffractive optical member) includes a diffractive member 42 having a diffractive function and a light collecting member 43 having a light collecting function. It is sufficient if the diffractive member 42 includes, for example, a transmissive volume hologram diffraction grating, and it is sufficient if the light collecting member 43 includes, for example, a hologram lens. Alternatively, the diffractive member 42 and the light collecting member 43 can include one member. Furthermore, regarding the order of arrangement of the diffractive member 42 and the light collecting member 43, the light collecting member 43 may be arranged on the observer side or the diffractive member 42 may be arranged on the observer side.

The projection light emitted from the transfer optical system (movable mirror) 22 is deflected by the diffractive member 42, changed in traveling angle (direction), incident on the light collecting member 43, collected by the light collecting member 43, and forms an image on the retina of the observer 50. On the other hand, part of the infrared light emitted from the light emitting unit 33C is reflected by the diffractive member 42 (or the retroreflective marker 41 attached to the diffractive member 42) and is incident on the light receiving unit 34C. Furthermore, the rest of the infrared light emitted from the light emitting unit 33C is deflected by the diffractive member 42, changed in traveling angle (direction), and is incident on the light collecting member 43. The light is not collected by the light collecting member 43 (that is, not affected by the light collecting member 43), but passes through the light collecting member 43, collides with the pupil 51 of the observer 50, is reflected by the pupil 51 of the observer 50, passes through the light collecting member 43, is deflected by the diffractive member 42, changed in traveling angle (direction), and is incident on the light receiving unit 34C. Note that, in FIG. 6, the infrared light emitted from the light emitting unit 33C and returning to the light receiving unit 34C is indicated by black arrows, and the luminous flux of visible light (image) emitted from the transfer optical system (movable mirror) 22 is indicated by different blank arrows.

In a case where a lens member including a general optical glass is used as the eyepiece optical system 40C, there is no wavelength selectivity, all visible light is collected and reaches the retina of the observer 50, and therefore the observer can observe only a projected image and cannot observe the outside scene. Furthermore, the pupil 51 of the observer 50 cannot be detected from the second position detection apparatus 32 through the eyepiece optical system 40C, and the arrangement position of the second position detection apparatus 32 is greatly restricted.

The wavelength selectivity of the light collecting function is required to act only on the wavelength of the light emitted from the image forming apparatus 21. When the wavelength selectivity of the light collecting function is weakened and the light other than the wavelength of the light emitted from the image forming apparatus 21 (for example, the light of the outside scene) is collected by the eyepiece optical system 40C, the observer 50 can hardly observe the outside scene, and there is a possibility that it becomes difficult to recognize the position of the pupil 51 of the observer 50 by the light receiving unit 34C. On the other hand, the wavelength selectivity of the diffractive function is required to act not only on the wavelength of the light emitted from the image forming apparatus 21, but also on a wavelength used for detecting the position of the pupil 51 of the observer 50 (for example, in a case where an infrared camera is used, the wavelength of infrared light). Therefore, in some cases, the diffractive member 42 may include a plurality of diffractive members having wavelength selectivity, and the light collecting member 43 may include a plurality of light collecting members having wavelength selectivity.

The wavelength range and whether or not the diffractive function and the light collecting function need to act are summarized in Table 1. By imparting such an optical function to the eyepiece optical system 40C, the degree of freedom in installing the image display apparatus 20 is increased, and the observer can superimpose an image with a landscape for observation, and at the same time, the pupil 51 of the observer 50 can be detected through the eyepiece optical system 40C by the second position detection apparatus 32.

TABLE 1

|  | Example of wavelength | Diffractive function | Light collecting function |
|---|---|---|---|
| Transfer optical system (picture light source) | Around λ = 450 nm<br>Around λ = 520 nm<br>Around λ = 640 nm | Work<br>Work<br>Work | Work<br>Work<br>Work |
| Second position detection apparatus | Around λ = 850 nm | Work | Does not work |
| Other (outside scene or the like) | Other than those above | Does not work | Does not work |

Figure 12A:
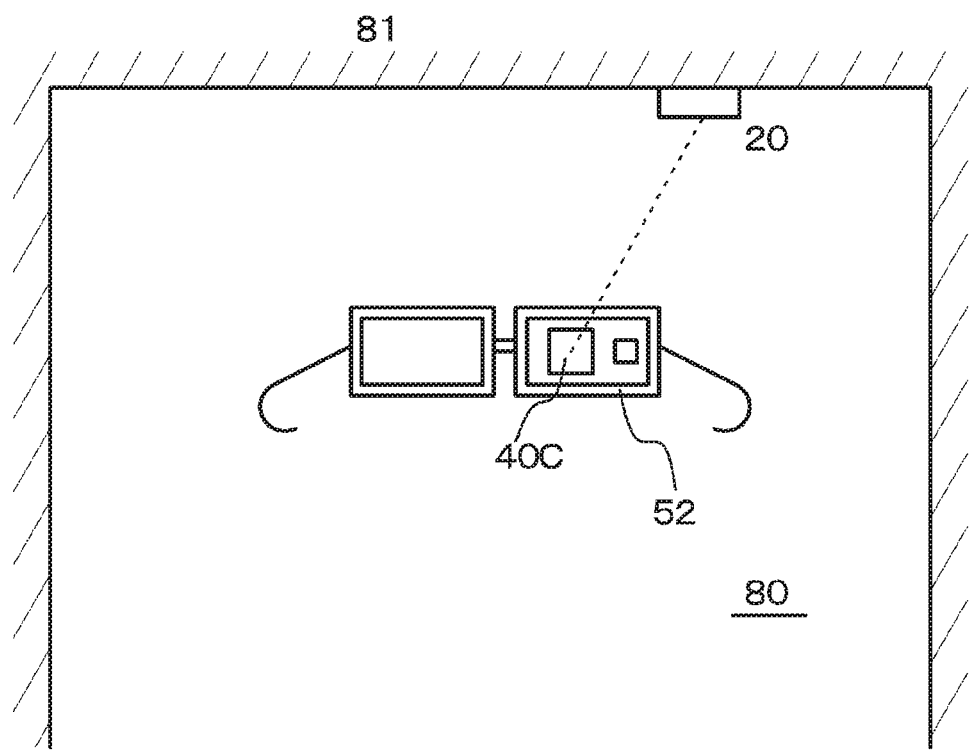
FIGS. 12A and 12B are schematic diagrams showing a state in which the display apparatus of Example 3 is used indoors and a state in which an image forming apparatus is arranged behind a seat back.

FIG. 12A shows a usage example of the display apparatus of Example 3, and FIG. 12A is a schematic view of a state where the display apparatus of Example 3 is used indoors. The image display apparatus 20 is arranged on a wall surface 81 of a room 80. When the observer 50 stands at a predetermined position in the room 80, the image from the image display apparatus 20 reaches the eyepiece optical system 40C, and the observer 50 can observe this image via the eyepiece optical system 40C.

Figure 12B:
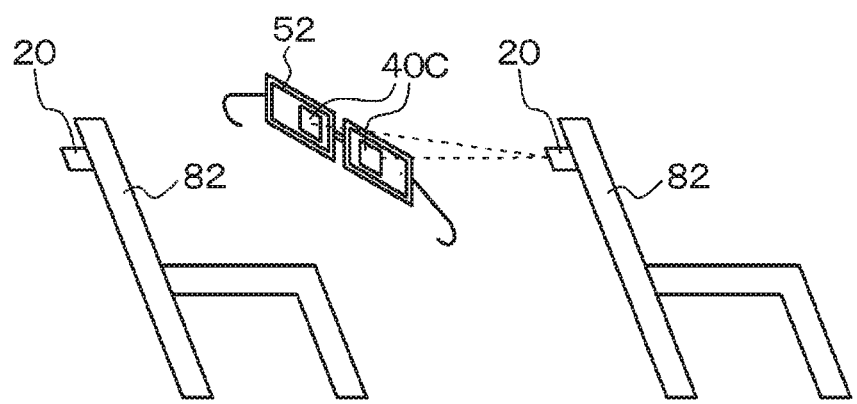

Alternatively, another usage example of the display apparatus of Example 3 is shown in FIG. 12B, which is a schematic diagram of a state in which the image display apparatus 20 constituting the display apparatus of Example 3 is arranged on the back surface of the back (backrest) of a seat 82 and used. When the observer is seated in the seat 82 on a back side, an image is emitted from the image display apparatus 20 arranged on the back surface of the back of the seat 82 on a front side toward the eyepiece optical system 40C mounted on the observer, and reaches the eyepiece optical system 40C, so that the observer 50 can observe this image via the eyepiece optical system 40C. More specifically, there is an example in which the image forming apparatus for a passenger is attached to the back surface of the back (backrest) of a seat of a vehicle or an aircraft, or an example in which the image forming apparatus for audience is attached to the back surface of the back (backrest) of a seat in a theater or the like. Note that the usage examples of the display apparatus described above can be applied to other examples.

Example 4

Figure 7A:
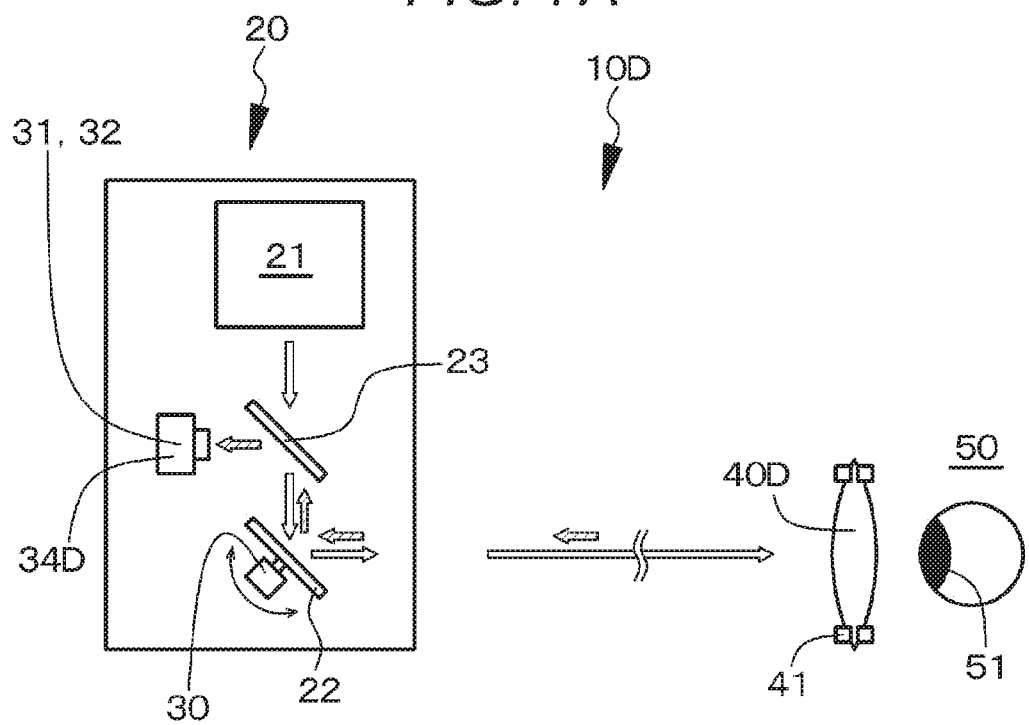
FIGS. 7A and 7B are conceptual diagrams of a display apparatus of Example 4 and a variation example thereof.
Figure 7B:
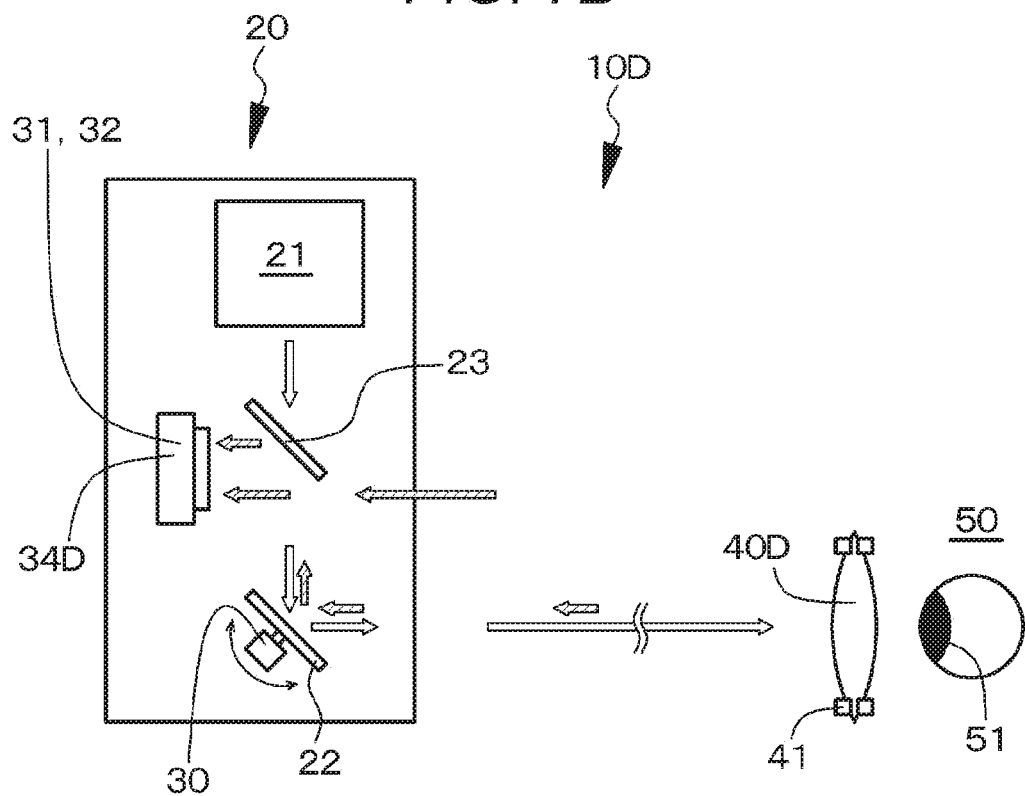

Example 4 is a variation of Examples 1 to 3. As shown in the conceptual diagram of FIG. 7A, in a display apparatus 10D of Example 4, the luminous flux emitted from an image forming apparatus 21 passes through a half mirror 23 and is incident on a transfer optical system 22. Furthermore, the light (visible light) reflected by an eyepiece optical system 40D and the pupil 51 of the observer 50 is incident on a light receiving unit 34D constituting the first position detection apparatus 31 and the second position detection apparatus 32 via the transfer optical system 22 and the half mirror 23. With such a structure, since the periphery of the head of the observer 50 can be recognized through the transfer optical system 22, it is possible to cover the entire spatial range in which the transfer optical system 22 can project. Since the origin of the coordinate system of the transfer optical system 22 and the origin of the coordinate system of the first position detection apparatus 31 and the second position detection apparatus 32 match each other, the initial calibration can be simplified and a positional misalignment with respect to various fluctuations can be suppressed. Note that, in FIGS. 7A and 7B, the detection light returning to the light receiving unit 34D via the transfer optical system 22 and the half mirror 23 is shown by blank arrows with a hatching line, and the luminous flux of the visible light (image) emitted from the transfer optical system (movable mirror) 22 is shown by blank arrows.

By the way, since the eyepiece optical system 40D and the pupil 51 of the observer 50 are detected via the transfer optical system 22, the detected coordinates are not absolute coordinates, but relative coordinates. Therefore, in a case where the sight of the observer 50 is lost, there is a possibility that it becomes unclear in which direction the transfer optical system 22 should be directed. In order to cope with such a phenomenon, it is sufficient if another camera for detecting the observer 50 is arranged outside the transfer optical system 22 for absolute coordinate recognition. Since such a camera does not require high performance with respect to resolution and capturing speed, a relatively inexpensive camera can be used. Alternatively, in addition to the configuration described with reference to FIG. 7A, as shown in a conceptual diagram in FIG. 7B, the light receiving unit (camera) 34D may be arranged so that an image around the head of the observer 50 can be directly obtained. Note that, in FIG. 7B, light received by the light receiving unit 34D without passing through the transfer optical system 22 and the half mirror 23 is indicated by a blank arrow with a hatching line.

Alternatively, a method of controlling the transfer optical system (movable mirror) 22 may include two types: a tracking mode and a search mode. When the position of the observer 50 is unknown, the search mode is set, and the movable range of the transfer optical system 22 is two-dimensionally scanned to search for the observer 50, the position of the observer 50 is specified, and thereafter, the mode is switched to the tracking mode so as to control the transfer optical system (movable mirror) 22 described in Example 1.

The light emitting unit may be arranged outside the transfer optical system 22 to illuminate the entire head of the observer 50, and although not shown, the luminous flux emitted from the image forming apparatus 21 and the luminous flux emitted from the light emitting unit may be combined by the half mirror 23 so that the resulting luminous flux is incident on the transfer optical system 22 and emitted toward the eyepiece optical system 40D. Alternatively, a structure may be employed in which a light emitting unit for detection light is prepared in the image forming apparatus 21 and light is incident on the transfer optical system 22 and is emitted toward the eyepiece optical system 40D.

Example 5

Figure 8A:
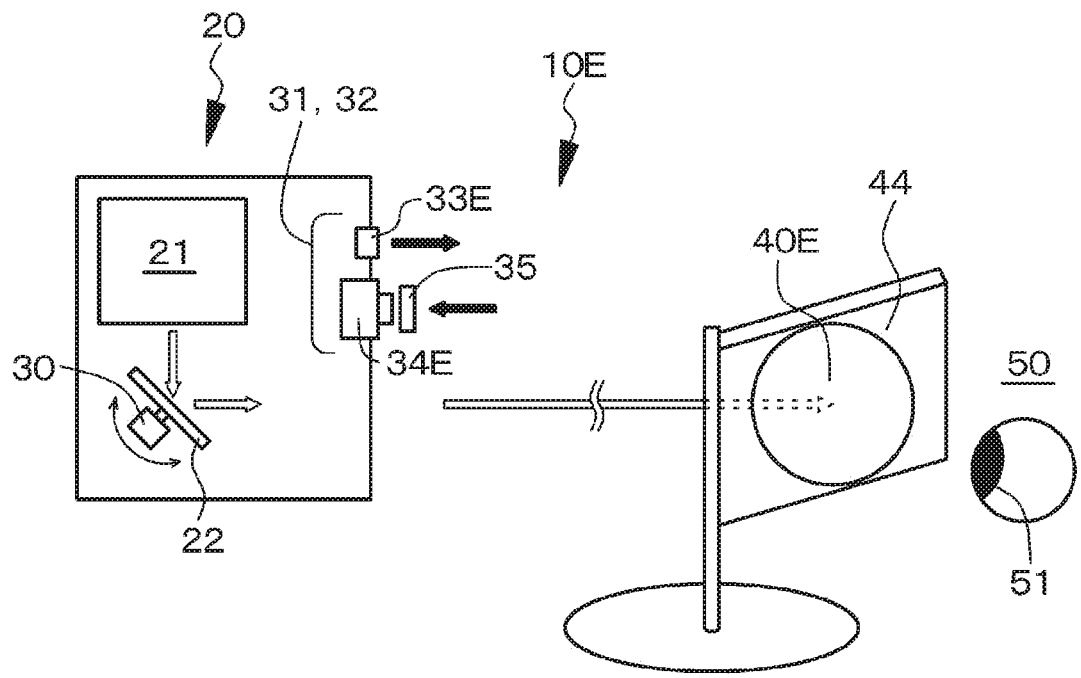
FIGS. 8A and 8B are conceptual diagrams of a display apparatus of Example 5 and a variation example thereof.

Example 5 is a variation of Example 3 and its variation example. As shown in the conceptual diagram of FIG. 8A, in a display apparatus 10E of Example 5, an eyepiece optical system 40E and the image display apparatus 20 are relatively movable (that is, the image display apparatus 20 is arranged at a location distant from the observer 50), and the eyepiece optical system 40E is arranged at a location distant from the observer 50. That is, the eyepiece optical system 40E is not mounted on the observer 50. The eyepiece optical system 40E is of a stationary type and is held by a holding member 44, or is incorporated into the holding member 44 integrally with the holding member 44. When carried, the holding member 44 and the eyepiece optical system 40E are folded and stored, and the eyepiece optical system 40E is assembled when the display apparatus 10E is used. It is sufficient if position adjustment is performed during assembly of the transfer optical system 22 and the eyepiece optical system 40E, and the positional relationship does not change during use. The image emitted from the image forming apparatus 21 reaches the pupil 51 of the observer 50 via the eyepiece optical system 40E. Examples of such a display apparatus 10E of Example 5 include a retina projection type mini monitor. The eyepiece optical system 40E has a configuration and structure similar to those of the eyepiece optical system 40C described in Example 3, and the light emitting unit 33E and the light receiving unit 34E have a configuration and structure similar to those of the light emitting unit 33C and the light receiving unit 34C.

Figure 8B:
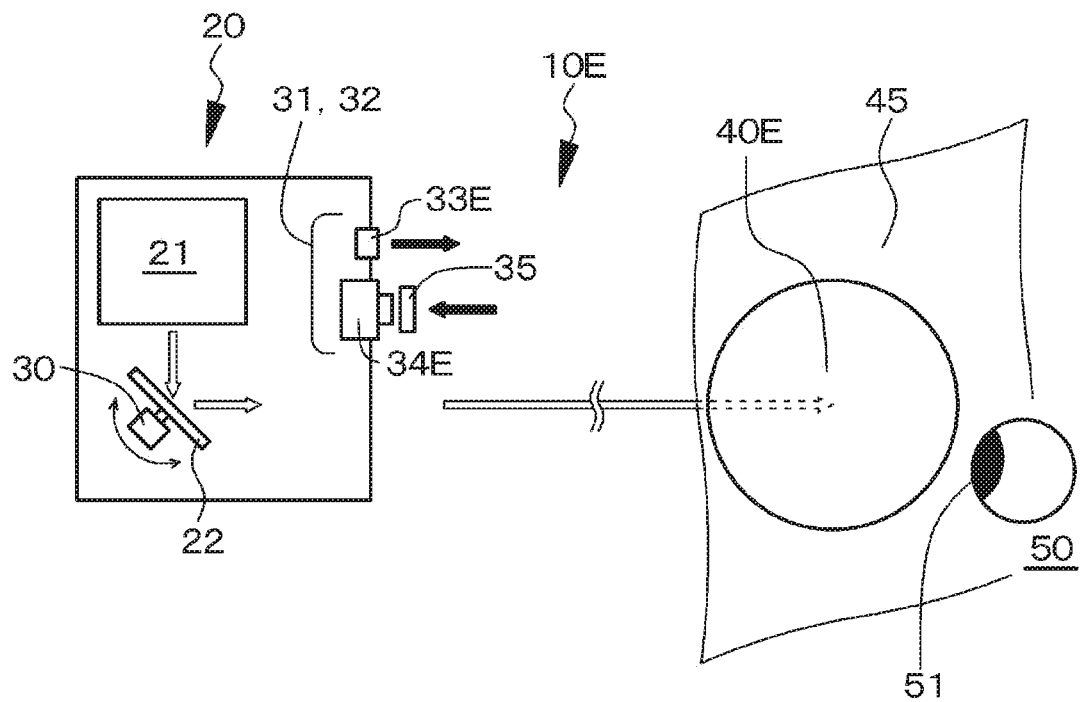

Alternatively, as shown in the conceptual diagram in FIG. 8B, the stationary eyepiece optical system 40E is incorporated in a glass window 45 or an exhibition window of a museum, an art gallery, an observatory, an aquarium, or the like, a windshield for an automobile, a full-face helmet, a protective face, or the like. Also in this case, the positions of the transfer optical system 22 and the eyepiece optical system 40E do not change, and the image emitted from the image forming apparatus 21 reaches the pupil 51 of the observer 50 via the eyepiece optical system 40E.

Example 6

Example 6 is a variation of Examples 1 to 5. Formulae (4-1), (4-2), (7-1), and (7-2) described above represent the position of the projection light in the eyepiece optical system. Here, when the value of the relative positional misalignment amount of the image (the misalignment amount of the observer's pupil with respect to the eyepiece optical system) $d_0$ is constant, as the focal length $f_0$ of the eyepiece optical system 40F is increased, the value of $\theta_2$ (or projection angle $\theta_1$) can be reduced. In other words, the greater the focal length $f_0$ of an eyepiece optical system 40F, the greater the misalignment amount do that can be accommodated. Therefore, it is possible to increase the value of the controllable misalignment amount $d_0$ without breaking the ideal conditions.

Figure 9A:
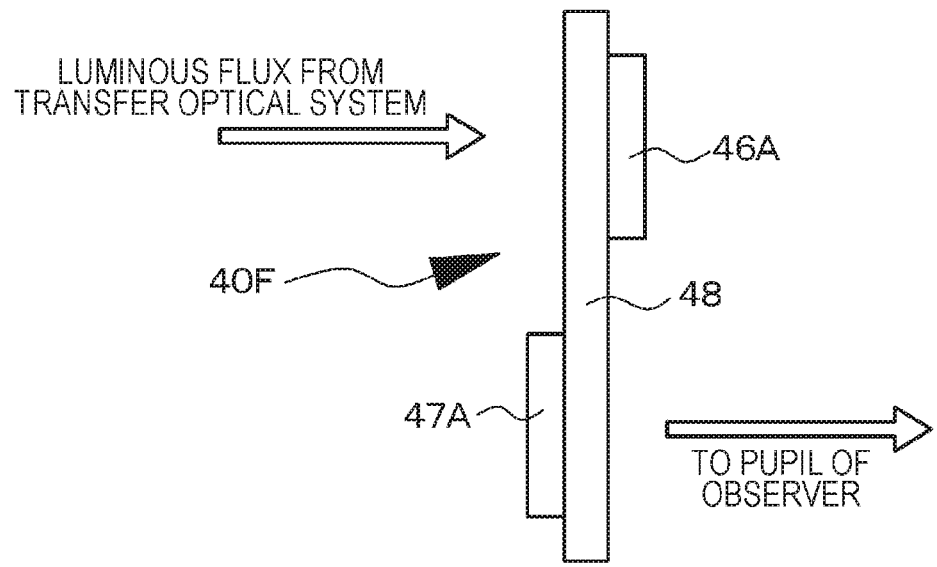
FIGS. 9A and 9B are conceptual diagrams of a display apparatus of Example 6.
Figure 9B:
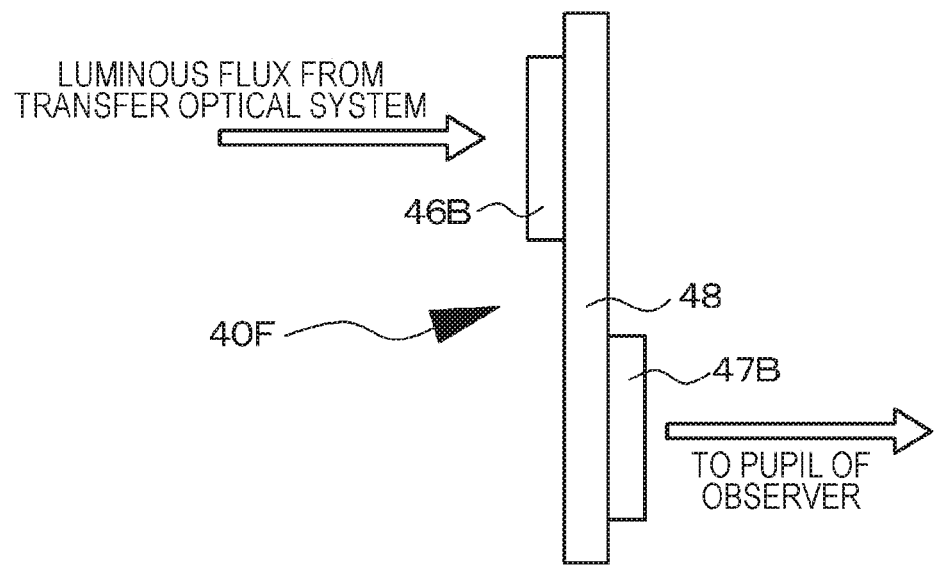

As shown in the conceptual diagram of the eyepiece optical system 40F in FIGS. 9A and 9B, in the display apparatus of Example 6, the eyepiece optical system 40F includes a light collecting member 46A, 46B on which an image from the transfer optical system 22 is incident and a deflection member 47A, 47B that guides the light emitted from the light collecting member 46A, 46B to the pupil 51 of the observer 50. The image from the transfer optical system 40F is changed in propagation and transfer direction in the direction of the deflection member 47A, 47B in the light collecting member 46A, 46B. The light collecting member 46A, 46B and the deflection member 47A, 47B are not limited, but are attached to a support member 48, or provided on the support member 48 integrally with the support member 48. In this way, the light collecting member 46A, 46B and the deflection member 47A, 47B are combined and the optical path is turned back so as to extend the focal length $f_0$. Note that, as shown in FIG. 9A, the light collecting member 46A includes a reflective hologram lens and the deflection member 47A includes a reflective volume hologram diffraction grating, or, as shown in FIG. 9B, the light collecting member 46B includes a transmissive hologram lens and the deflection member 47B includes a transmissive volume hologram diffraction grating. However, the light collecting member and the deflection member are not limited to the above. Furthermore, the light from the light collecting member may be totally reflected once or more within the support member and may be incident on the deflection member.

Example 7

Figure 10:
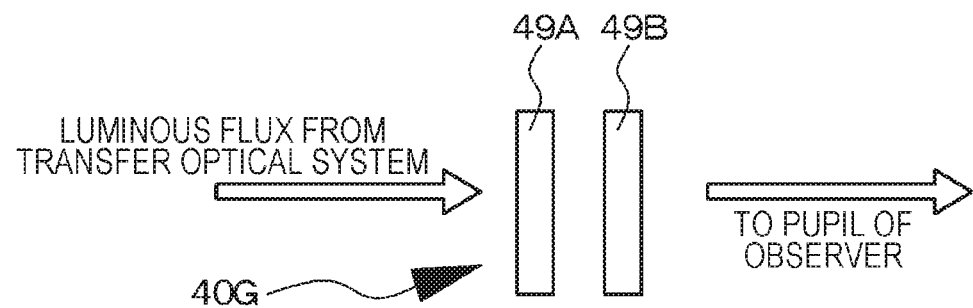
FIG. 10 is a conceptual diagram of a display apparatus of Example 7.

Example 7 is a variation of Examples 1 to 6. As shown in the conceptual diagram of FIG. 10, in the display apparatus of Example 7, an eyepiece optical system 40G includes a diffraction grating 49B, and further includes a light collecting member 49A on the light incident side. Note that the light collecting member 49A may be provided between the diffraction grating 49B and the pupil 51 of the observer 50. Then, in this way, a structure equivalent to that in which a plurality of focal points of the eyepiece optical system 40G is present can be obtained. That is, for example, even in a case where the image emitted from the transfer optical system 22 described in Example 1 does not reach the pupil 51 of the observer 50 due to various reasons, not a 0th-order diffraction light of the diffraction grating 49A, but, for example, a 1st-order diffraction light, a −1st-order diffraction light, or the like reaches the pupil 51 of the observer 50, thereby achieving a system having higher robustness for the observer 50. That is, it is possible to achieve a more robust display apparatus while reducing the burden on the observer 50. Furthermore, since a plurality of focal points can be prepared, it is possible to enlarge the range in which the observer 50 can observe the image even in a case where the value of $\theta_2$ (or projection angle $\theta_1$) is large.

It is possible to exemplify a form in which the diffraction grating 49B divides the image into three images in the horizontal direction, a form in which the diffraction grating 49B divides the image into three images in the vertical direction, a form in which the diffraction grating 49B divides the image into three images in the horizontal direction and three images in the vertical direction into a cross (form in which one image including the center light path overlaps and the image is divided into five images in total), a form in which the diffraction grating 49B divides the image into two images in the horizontal direction and two images in the vertical direction, 2×2=4, and a form in which the diffraction grating 49B divides the image into three images in the horizontal direction and three images in the vertical direction, 3×3=9.

Example 8

Example 8 is a variation of Examples 1 to 7. In the display apparatus of Example 8, on the basis of the positional information of an eyepiece optical system 40H detected by the first position detection apparatus 31 and the positional information of the pupil 51 of the observer 50 detected by the second position detection apparatus 32, the position of the image formed in the image forming apparatus 21 is corrected.

In Example 8, in the image forming apparatus, an image is formed in a region smaller than the entire image forming region. For example, when the entire image forming region is 1×1, the region where an image is formed is (p×q). Here, 0<p<1 and 0<q<1.

As shown in the conceptual diagram of FIGS. 11A, 11B, 11C, and 11D, the outer edge of the image in a case where an image is formed on the basis of the region (1×1) of the entire image forming region is indicated by two-dot chain lines, the light from the center of the image in a case where an image is formed on the basis of the region (1×1) is indicated by chain lines, and the outer edge of the image in a case where an image is formed on the basis of an image forming region (p×q) is indicated by broken lines. In the illustrated example, p=q=0.5, and when the length (size) of one side of the image formed on the basis of the region (1×1) of the entire image forming region is $i_0$, the length (size) of one side of the image formed on the basis of the region (p×q) is $i_0/2$.

Figure 11A:
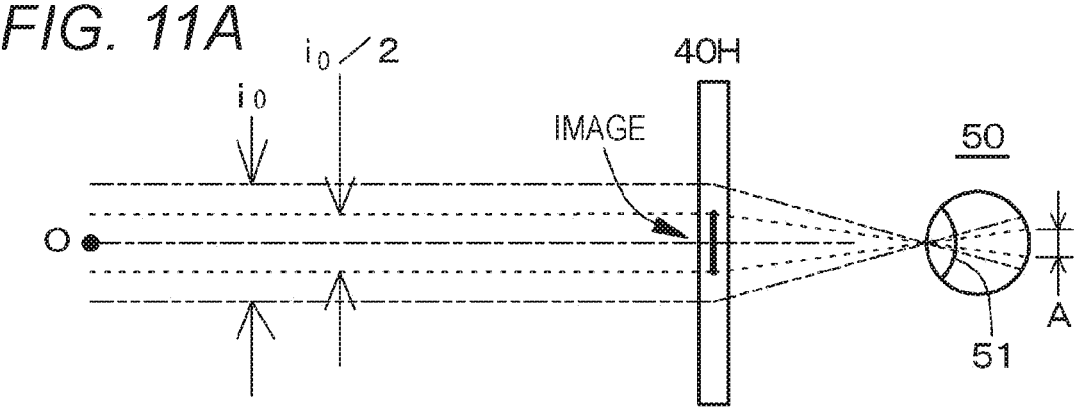
FIGS. 11A, 11B, 11C and 11D are diagrams schematically showing behavior of a luminous flux emitted from a transfer optical system, and a positional relationship between an eyepiece optical system and an observer's pupil in the display apparatus of Example 8.
Figure 11B:
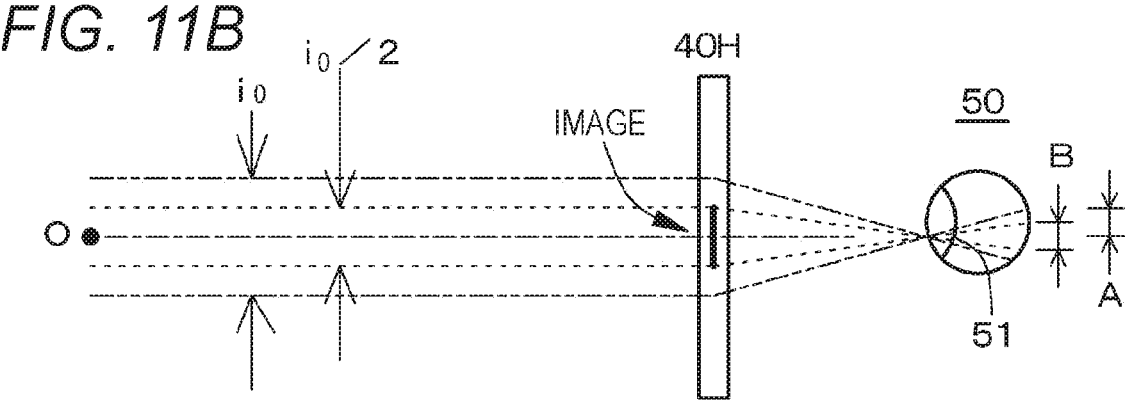
Figure 11C:
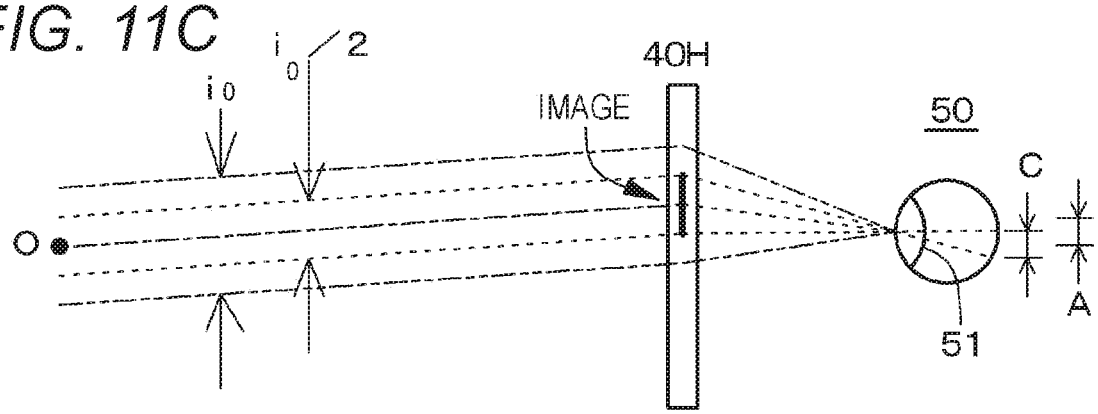

It is assumed that the pupil 51 of the observer 50 has moved upward in the drawing from the state shown in FIG. 11A, as shown in FIG. 11B. An image observed by the observer 50 in the state shown in FIG. 11A is schematically indicated by an arrow "A", and an image observed by the observer 50 in the state shown in FIG. 11B is schematically indicated by an arrow "B". The image observed by the observer 50 moves to the lower part of the retina from the state of arrow "A" to the state of arrow "B". As described above, a change in the relative position between the eyepiece optical system 40H and the pupil 51 of the observer 50 causes movement of the image on the retina observed by the observer 50, as shown in FIGS. 11A and 11B. Then, in such a case, as shown in FIG. 11C and as described in Examples 1 to 7, on the basis of the positional information of the eyepiece optical system detected by the first position detection apparatus and the positional information of the pupil 51 of the observer 50 detected by the second position detection apparatus, the transfer optical system controlling apparatus controls the transfer optical system such that the image incident from the image forming apparatus reaches the eyepiece optical system, that is, the image incident from the image forming apparatus is formed on the retina of the observer 50 via the eyepiece optical system. The image observed by the observer 50 in the state shown in FIG. 11C is schematically shown by the arrow "C", and the image observed by the observer 50 remains moved the lower part of the retina from the state of the arrow "A" to the state of the arrow "C".

Figure 11D:
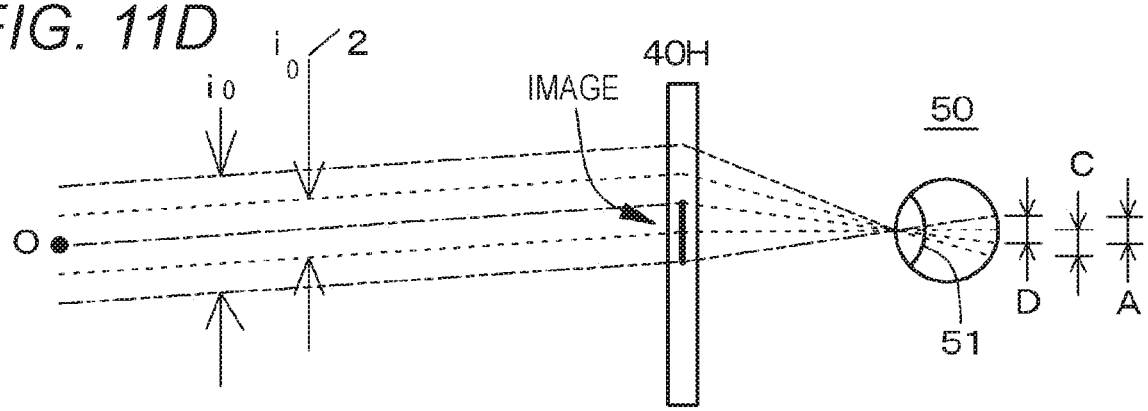

Therefore, on the basis of the positional information of the eyepiece optical system 40H detected by the first position detection apparatus 31 and the positional information of the pupil 51 of the observer 50 detected by the second position detection apparatus 32, the position of the image formed in the image forming apparatus 21 is corrected. Specifically, as shown in FIG. 11D, the region (p×q) is moved to an appropriate position in the image forming apparatus 21 and an image is formed such that the image on the retina does not move or the image on the retina is moved as little as possible when the observer 50 observes the image formed on the basis of the region (p×q). For example, in a case where the image is formed in a central region of the image forming apparatus 21 (see FIGS. 11A, 11B and 11C), the image forming position in the image forming apparatus 21 is corrected such that the image is formed in the region above the image forming apparatus 21 as shown in FIG. 11D (the image emitted from the transfer optical system is emitted from the lower part of the transfer optical system). An image observed by the observer 50 in the state shown in FIG. 11D is schematically shown by an arrow "D". That is, the image forming position in the image forming apparatus 21 is displaced in a direction of canceling the relative positional misalignment between the eyepiece optical system 40H and the pupil 51 of the observer 50. Accordingly, it is possible to more unfailingly suppress the movement of the image on the retina observed by the observer 50 as much as possible, and it is possible to fix the display position of the image with respect to the observer's field of view as much as possible.

The display apparatus of the present disclosure has been described above on the basis of preferred examples, but the display apparatus of the present disclosure is not limited to these examples. The configuration and structure of the display apparatus, and the configuration and structure of the image display apparatus, the image forming apparatus, the transfer optical system, or the eyepiece optical system can be changed as appropriate. For example, in a case where the observer is in an inappropriate place as viewed from the display apparatus, the display apparatus may perform guiding for guiding the observer to an appropriate place by voice or image and picture. The display apparatus may include a plurality of image forming apparatuses. That is, the display apparatus can include a plurality of image forming apparatuses having different positions for emitting images, and the plurality of image forming apparatuses may emit the same image, and one of these plurality of images may be received by one eyepiece optical system. Then, in this way, the degree of freedom of the relative positional relationship between the image forming apparatus and the observer can be increased. That is, for example, when the observer is located at a predetermined position, the image from the image forming apparatus reaches the eyepiece optical system, and the observer can observe this image through the eyepiece optical system, and this predetermined position can be expanded.

Note that the present disclosure may adopt the configuration described below.

[A01]<<Display Apparatus: First Aspect>>

A display apparatus including:

an eyepiece optical system; and an image display apparatus including an image forming apparatus and a transfer optical system that emits an image incident from the image forming apparatus to the eyepiece optical system, in which the eyepiece optical system and the image display apparatus are arranged to be spatially separated from each other, the eyepiece optical system forms an image from the transfer optical system on a retina of an observer, the image display apparatus further includes a first position detection apparatus that detects a position of the eyepiece optical system, a second position detection apparatus that detects a position of a pupil of the observer, and a transfer optical system controlling apparatus, and on the basis of positional information of the eyepiece optical system detected by the first position detection apparatus and positional information of the pupil of the observer detected by the second position detection apparatus, the transfer optical system controlling apparatus controls the transfer optical system such that the image incident from the image forming apparatus reaches the eyepiece optical system.

[A02] The display apparatus according to [A01], in which the eyepiece optical system and the image display apparatus are relatively movable.

[A03] The display apparatus according to [A01] or [A02], in which the eyepiece optical system is mounted on the observer.

[A04] The display apparatus according to [A01] or [A02], in which the eyepiece optical system is arranged at a location distant from the observer.

[A05] The optical apparatus according to any one of [A01] to [A04], in which the transfer optical system includes a movable mirror.

[A06] The display apparatus according to any one of [A01] to [A05], in which when an angle formed by a straight line connecting a center of the eyepiece optical system and a center of the pupil of the observer and a normal line passing through the center of the eyepiece optical system is $\theta_1$, an angle formed by a light beam emitted from a center of the image forming apparatus passing through the transfer optical system, and reaching the eyepiece optical system and a normal line passing through the center of the eyepiece optical system is $\theta_2$, and a focal length of the eyepiece optical system is $f_0$ (unit: mm), the transfer optical system controlling apparatus controls the transfer optical system so as to satisfy $$f_0 \cdot |\tan(\theta_2) - \tan(\theta_1)| \le 3.5.$$

[A07] The display apparatus according to any one of [A01] to [A06], in which the second position detection apparatus includes a light emitting unit that emits infrared light and a light receiving unit that receives the infrared light reflected by the pupil of the observer, and the eyepiece optical system has a wavelength-dependent light-collecting characteristic.

[A08] The display apparatus according to [A07], in which the infrared light emitted from the light emitting unit is not affected by the light-collecting characteristic of the eyepiece optical system.

[A09] The optical apparatus according to [A07] or [A08], in which a retroreflective marker is attached to the eyepiece optical system.

[A10] The display apparatus according to any one of [A07] to [A09], in which the eyepiece optical system includes a hologram lens.

[A11] The display apparatus according to any one of [A01] to [A06], in which the second position detection apparatus includes a light receiving unit that receives visible light reflected by the pupil of the observer.

[A12] The display apparatus according to [A11], in which the eyepiece optical system has a wavelength-dependent light-collecting characteristic.

[A13] The display apparatus according to [A11], in which the eyepiece optical system includes a lens member.

[A14] The display apparatus according to [A11] or [A12], in which the eyepiece optical system includes a hologram lens.

[A15] The display apparatus according to any one of [A01] to [A06], in which the second position detection apparatus includes a light emitting unit that emits infrared light and a light receiving unit that receives the infrared light reflected by the pupil of the observer, and the eyepiece optical system has a wavelength-dependent diffraction characteristic.

[A16] The display apparatus according to [A15], in which the infrared light emitted from the light emitting unit is affected by the diffraction characteristic of the eyepiece optical system.

[A17] The display apparatus according to [A16], in which the infrared light emitted from the light emitting unit is not affected by the light-collecting characteristic of the eyepiece optical system.

[A18] The display apparatus according to any one of [A15] to [A17], in which the eyepiece optical system includes a diffractive optical member.

[A19] The display apparatus according to [A18], in which the diffractive optical member includes a diffractive member having a diffractive function and a light collecting member having a light collecting function.

[A20] The display apparatus according to any one of [A01] to [A19], in which the eyepiece optical system includes a light collecting member on which an image from the transfer optical system is incident, and a deflection member that guides light emitted from the light collecting member to the pupil of the observer.

[A21] The optical apparatus according to any one of [A01] to [A20], in which the first position detection apparatus emits infrared light.

[A22] The display apparatus according to any one of [A01] to [A21], in which on the basis of positional information of the eyepiece optical system detected by the first position detection apparatus and positional information of the pupil of the observer detected by the second position detection apparatus, a position of an image formed in the image forming apparatus is corrected.

[A23] The display apparatus according to any one of [A01] to [A22], in which the eyepiece optical system includes a diffraction grating.

[A24]<<Display Apparatus: Second Aspect>>

A display apparatus including:

an eyepiece optical system; and an image display apparatus including an image forming apparatus and a transfer optical system that emits an image incident from the image forming apparatus to the eyepiece optical system, in which the eyepiece optical system and the image display apparatus are arranged to be spatially separated from each other, the eyepiece optical system forms an image from the transfer optical system on a retina of an observer, the image display apparatus further includes a first position detection apparatus that detects a position of the eyepiece optical system, a second position detection apparatus that detects a position of a pupil of the observer, and a transfer optical system controlling apparatus, and the second position detection apparatus is arranged at a position where the pupil of the observer can be seen (detected).

REFERENCE SIGNS LIST 10A, 10B, 10C, 10D, 10E Display apparatus
20 Image display apparatus
21, 21a, 21b, 21c Image forming apparatus
22 Transfer optical system (movable mirror)
23 Half mirror
30 Transfer optical system controlling apparatus
31 First position detection apparatus
32 Second position detection apparatus
33A, 33C, 33E Light emitting unit
34A, 34B, 34C, 34D, 34E Light receiving unit
35 Filter (infrared transmission filter)
40A,40B,40C,40D,40E,40F,40G,40H Eyepiece optical system
41 Retroreflective marker
42 Light collecting member
43 Diffractive member
44 Holding member
45 Glass window 46, 46A, 46B Light collecting member
47, 47A, 47B Deflection member
48 Support member
49A Light collecting member
49B Diffraction grating
50 Observer
51 Pupil
52 Frame
60 Housing
61 Light source
62 Polarization beam splitter
63 Liquid crystal display apparatus (LCD)
64 Optical system
65 Organic EL display apparatus
66 Convex lens
71 Light source
72 Collimating optical system
73 Total reflection mirror
74 Scanning means
75 Relay optical system
80 Room
81 Wall surface
82 Seat

What is claimed is:

1. A display apparatus, comprising:
an eyepiece optical system arranged at a location distant from an observer; and
an image display apparatus including an image forming apparatus and a transfer optical system that emits an image incident from the image forming apparatus to the eyepiece optical system, wherein
the eyepiece optical system and the image display apparatus are arranged to be spatially separated from each other,
the eyepiece optical system forms an image from the transfer optical system on a retina of the observer,
the image display apparatus further includes
a first position detection apparatus that detects a position of the eyepiece optical system,
a second position detection apparatus that detects a position of a pupil of the observer, and
a transfer optical system controlling apparatus, and
on a basis of positional information of the eyepiece optical system detected by the first position detection apparatus and positional information of the pupil of the observer detected by the second position detection apparatus, the transfer optical system controlling apparatus controls the transfer optical system such that the image incident from the image forming apparatus reaches the eyepiece optical system.

2. The display apparatus according to claim 1, wherein the eyepiece optical system and the image display apparatus are relatively movable.

3. The display apparatus according to claim 1, wherein the eyepiece optical system is mounted on the observer.

4. The display apparatus according to claim 1, wherein the transfer optical system includes a movable mirror.

5. The display apparatus according to claim 1, wherein when an angle formed by a straight line connecting a center of the eyepiece optical system and a center of the pupil of the observer and a normal line passing through the center of the eyepiece optical system is $\theta_1$, an angle formed by a light beam emitted from a center of the image forming apparatus passing through the transfer optical system, and reaching the eyepiece optical system and a normal line passing through the center of the eyepiece optical system is $\theta_2$, and a focal length of the eyepiece optical system is $f_0$ (unit: mm), the transfer optical system controlling apparatus controls the transfer optical system so as to satisfy $$f_0 \cdot |\tan(\theta_2) - \tan(\theta_1)| \leq 3.5.$$

6. The display apparatus according to claim 1, wherein
the second position detection apparatus includes a light emitting unit that emits infrared light and a light receiving unit that receives the infrared light reflected by the pupil of the observer, and
the eyepiece optical system has a wavelength-dependent light-collecting characteristic.

7. The display apparatus according to claim 6, wherein a retroreflective marker is attached to the eyepiece optical system.

8. The display apparatus according to claim 6, wherein the eyepiece optical system includes a hologram lens.

9. The display apparatus according to claim 1, wherein the second position detection apparatus includes a light receiving unit that receives visible light reflected by the pupil of the observer.

10. The display apparatus according to claim 9, wherein the eyepiece optical system has a wavelength-dependent light-collecting characteristic.

11. The display apparatus according to claim 1, wherein
the second position detection apparatus includes a light emitting unit that emits infrared light and a light receiving unit that receives the infrared light reflected by the pupil of the observer, and
the eyepiece optical system has a wavelength-dependent diffraction characteristic.

12. The display apparatus according to claim 11, wherein the infrared light emitted from the light emitting unit is affected by the diffraction characteristic of the eyepiece optical system.

13. The display apparatus according to claim 12, wherein the eyepiece optical system includes a diffractive optical member.

14. The display apparatus according to claim 13, wherein the diffractive optical member includes a diffractive member having a diffractive function and a light collecting member having a light collecting function.

15. The display apparatus according to claim 1, wherein the eyepiece optical system includes a light collecting member on which an image from the transfer optical system is incident, and a deflection member that guides light emitted from the light collecting member to the pupil of the observer.

16. The display apparatus according to claim 1, wherein the first position detection apparatus emits infrared light.

17. The display apparatus according to claim 1, wherein on a basis of positional information of the eyepiece optical system detected by the first position detection apparatus and positional information of the pupil of the observer detected by the second position detection apparatus, a position of an image formed in the image forming apparatus is corrected.

18. The display apparatus according to claim 1, wherein the eyepiece optical system includes a diffraction grating.

19. A display apparatus, comprising:
an eyepiece optical arranged at a location distant from an observer; and
an image display apparatus including an image forming apparatus and a transfer optical system that emits an image incident from the image forming apparatus to the eyepiece optical system, wherein
the eyepiece optical system and the image display apparatus are arranged to be spatially separated from each other, the eyepiece optical system forms an image from the transfer optical system on a retina of the observer,
the image display apparatus further includes
a first position detection apparatus that detects a position of the eyepiece optical system,
a second position detection apparatus that detects a position of a pupil of the observer, and
a transfer optical system controlling apparatus, and
the second position detection apparatus is arranged at a position where the pupil of the observer can be seen.

* * * * *